（12） United States Patent
Djebara et al.

(10) Patent No.: US 9,620,294 B2
(45) Date of Patent: Apr. 11, 2017

(54) WET ELECTROLYTIC CAPACITOR CONTAINING A RECESSED PLANAR ANODE AND A RESTRAINT

(71) Applicant: AVX Corporation, Fountain Inn, SC (US)

(72) Inventors: Lotfi Djebara, Paris (FR); James S. Bates, Saco, ME (US); Mitchell D. Weaver, Simpsonville, SC (US)

(73) Assignee: AVX Corporation, Fountain Inn, SC (US)

( * ) Notice: Subject to any disclaimer, the term of this patent is extended or adjusted under 35 U.S.C. 154(b) by 149 days.

(21) Appl. No.: 14/585,354

(22) Filed: Dec. 30, 2014

(65) Prior Publication Data

US 2016/0189876 A1    Jun. 30, 2016

(51) Int. Cl.
*H01G 9/15* (2006.01)
*H01G 9/145* (2006.01)
*H01G 9/048* (2006.01)
*H01G 9/042* (2006.01)
*A61N 1/39* (2006.01)
*H01G 9/052* (2006.01)

(52) U.S. Cl.
CPC ............ *H01G 9/145* (2013.01); *H01G 9/048* (2013.01); *A61N 1/3981* (2013.01); *H01G 9/042* (2013.01); *H01G 9/052* (2013.01)

(58) Field of Classification Search
CPC   H01G 9/15; H01G 9/08; H01G 9/025; H01G 9/06
See application file for complete search history.

(56) References Cited

U.S. PATENT DOCUMENTS

| 5,111,327 | A  | 5/1992  | Blohm et al.    |
|-----------|----|---------|-----------------|
| 5,369,547 | A  | 11/1994 | Evans           |
| 5,457,862 | A  | 10/1995 | Sakata et al.   |
| 5,473,503 | A  | 12/1995 | Sakata et al.   |
| 5,729,428 | A  | 3/1998  | Sakata et al.   |
| 5,812,367 | A  | 9/1998  | Kudoh et al.    |
| 6,197,252 | B1 | 3/2001  | Bishop et al.   |
| 6,322,912 | B1 | 11/2001 | Fife            |
| 6,391,275 | B1 | 5/2002  | Fife            |
| 6,416,730 | B1 | 7/2002  | Fife            |
| 6,527,937 | B2 | 3/2003  | Fife            |
| 6,576,099 | B2 | 6/2003  | Kimmel et al.   |
| 6,592,740 | B2 | 7/2003  | Fife            |
| 6,594,140 | B1 | 7/2003  | Evans et al.    |
| 6,635,729 | B1 | 10/2003 | Groenendaal et al. |
| 6,639,787 | B2 | 10/2003 | Kimmel et al.   |

(Continued)

*Primary Examiner* — Dion R Ferguson
(74) *Attorney, Agent, or Firm* — Dority & Manning, P.A.

(57) ABSTRACT

A wet electrolytic capacitor is provided. The capacitor includes a planar anode formed from a pressed and sintered powder, a cathode that includes a metal substrate that is coated with an electrochemically-active material, and a working electrolyte in communication with the planar anode and cathode. The planar anode has a recessed portion formed in at least one of its surfaces. The capacitor also includes at least one restraint that is in contact with the recessed portion and has a shape that generally corresponds with a shape of the recessed portion. The recessed portion of the planar anode allows for stabilization of the planar anode with via a restraint without increasing the dimensions of the capacitor.

24 Claims, 21 Drawing Sheets

(56) References Cited

U.S. PATENT DOCUMENTS

| | | | |
|---|---|---|---|
| 6,801,424 B1* | 10/2004 | Nielsen | H01G 9/08 361/517 |
| 6,987,663 B2 | 1/2006 | Merker et al. | |
| 7,085,126 B2 | 8/2006 | Muffoletto et al. | |
| 7,092,242 B1 | 8/2006 | Gloss et al. | |
| 7,220,397 B2 | 5/2007 | Kimmel et al. | |
| 7,341,705 B2 | 3/2008 | Schnitter | |
| 7,381,396 B2 | 6/2008 | Thomas et al. | |
| 7,419,926 B2 | 9/2008 | Schnitter et al. | |
| 7,483,260 B2 | 1/2009 | Ziarniak et al. | |
| 7,515,396 B2 | 4/2009 | Biler | |
| 8,279,585 B2 | 10/2012 | Dreissig et al. | |
| 2005/0190530 A1* | 9/2005 | Muffoletto | H01G 9/06 361/517 |
| 2005/0243501 A1* | 11/2005 | Muffoletto | H01G 9/06 361/534 |
| 2006/0279906 A1* | 12/2006 | Stemen | H01G 9/042 361/517 |
| 2012/0257327 A1* | 10/2012 | Zednickova | H01G 9/08 361/528 |
| 2012/0257329 A1* | 10/2012 | Biler | H01G 9/012 361/528 |

* cited by examiner

WET ELECTROLYTIC CAPACITOR CONTAINING A RECESSED PLANAR ANODE AND A RESTRAINT

BACKGROUND OF THE INVENTION

High voltage electrolytic capacitors are employed as energy storage reservoirs in many applications, including implantable medical devices. These capacitors are required to have a high energy density because it is desirable to minimize the overall size of the implanted device. This is particularly true of an implantable cardioverter defibrillator ("ICD"), also referred to as an implantable defibrillator, because the high voltage capacitors used to deliver the defibrillation pulse can occupy as much as one third of the ICD volume. Further, these capacitors experience high levels of shock and vibration conditions such that the capacitors must be adequately stabilized to prevent failure of the capacitors due to movement of, for example, a tantalum anode inside a casing of a wet electrolytic capacitor. Attempts have been made to stabilize the anodes of wet electrolytic capacitors by placing a restraint between the outer surface of the anode pellet and the casing wall. However, such an arrangement requires the use of a larger casing having an increased height in order to accommodate the restraint (e.g., a polymer, glass, or ceramic material), while at the same time still allowing enough room for the working electrolyte to create a sufficient connecting path between the anode and cathode of the capacitor. However, this defeats the purpose of utilizing a planar anode to reduce the overall size of the ICD and results in an undesirable increase in the overall size of the ICD. Further, there may not be sufficient contact between the anode surface and the restraint to effectively stabilize the anode within the capacitor casing.

As such, a need currently exists for an improved wet electrolytic capacitor for use in implantable medical devices, such as defibrillators.

SUMMARY OF THE INVENTION

In accordance with one embodiment of the present invention, a wet electrolytic capacitor is disclosed. The wet electrolytic capacitor includes a planar anode, a cathode, a restraint, and a working electrolyte. The planar anode includes an anodically oxidized pellet formed from a pressed and sintered powder, and the planar anode has a recessed portion formed in at least one surface. The cathode includes a metal substrate coated with an electrochemically-active material. The restraint is in contact with the recessed portion and has a shape that generally corresponds with a shape of the recessed portion. Further, the working electrolyte is in communication with the planar anode and the cathode.

In accordance with another embodiment of the present invention, a planar anode for a wet electrolytic capacitor is disclosed. The planar anode includes an anodically oxidized pellet formed from a pressed and sintered powder. A recessed portion is located in a surface of the planar anode, and the recessed portion is configured to receive a restraint.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
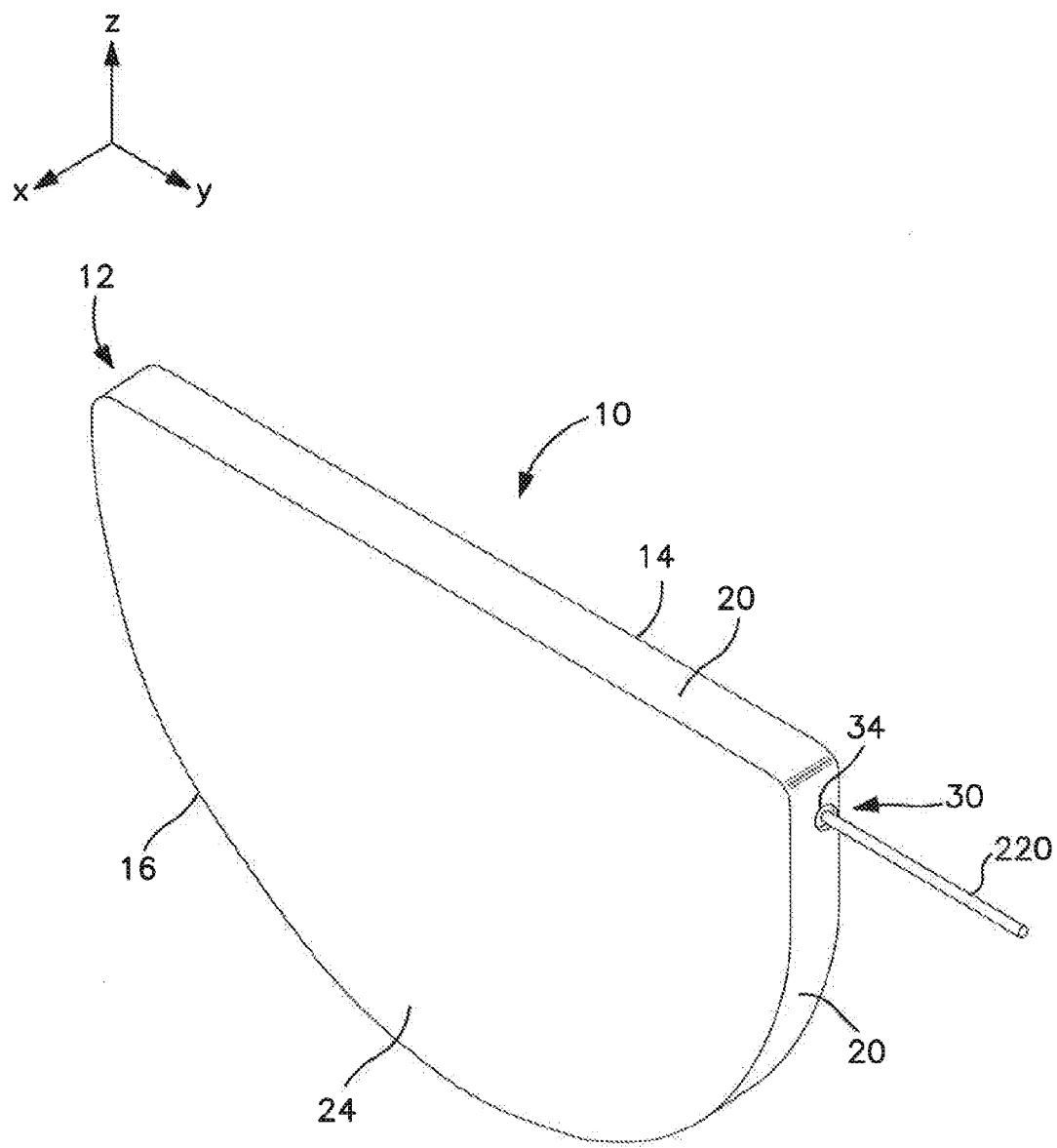
FIG. 1 is a perspective view of one embodiment of the wet electrolytic capacitor of the present invention.

Repeat use of reference characters in the present specification and drawings is intended to represent same or analogous features or elements of the invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is directed to a wet electrolytic capacitor that contains an anodically oxidized porous planar anode body, a cathode containing a metal substrate that is coated with an electrochemically-active material, and a working electrolyte that provides a connecting path between the planar anode and cathode. Further, a casing can surround the planar anode, and, in some embodiments, the metal substrate of the cathode forms the casing. The planar anode includes at least one recessed portion on at least one of its surfaces. Further, at least one restraint is positioned adjacent to and in contact with at least a part of the recessed portion of the planar anode. The recessed portion of the planar anode can be shaped to generally match the shape of the restraint such that the recessed portion of the planar anode can be locked into a secure position inside the casing by the restraint. In other words, the restraint and the recessed portion of the planar anode can have complimentary geometries to allow the restraint to fit into the recessed portion in order to stabilize the planar anode inside the casing. Thus, the shape of the recessed portion can generally correspond with the shape of the restraint with which it is in contact. Further, while one restraint can be in continuous contact with the entire recessed portion, it should be understood that this is not required, and one or more restraints can be utilized in a discontinuous manner so that one or more restraints are spaced apart from each other in the recessed portion. As a result of the arrangement of the capacitor where the planar anode is locked into place inside the casing by a restraint that fits into a recessed portion of the planar anode, the restraint can stabilize the planar anode when the capacitor is subjected to high levels of shock or vibration without increasing the overall dimensions of the capacitor.

Various embodiments of the present invention will now be described in more detail.

I. Planar Anode

The planar anode is typically formed from a valve metal composition. The specific charge of the composition may vary, such as from about 2,000 µF*V/g to about 80,000 µF*V/g, in some embodiments from about 5,000 µF*V/g to about 40,000 µF*V/g or more, and in some embodiments, from about 10,000 to about 20,000 µF*V/g. The valve metal composition contains a valve metal (i.e., metal that is capable of oxidation) or valve metal-based compound, such as tantalum, niobium, aluminum, hafnium, titanium, alloys thereof, oxides thereof, nitrides thereof, and so forth. For example, the valve metal composition may contain an electrically conductive oxide of niobium, such as niobium oxide having an atomic ratio of niobium to oxygen of 1:1.0±1.0, in some embodiments 1:1.0±0.3, in some embodiments 1:1.0±0.1, and in some embodiments, 1:1.0±0.05. The niobium oxide may be $NbO_{0.7}$, $NbO_{1.0}$, $NbO_{1.1}$, and $NbO_2$. Examples of such valve metal oxides are described in U.S. Pat. No. 6,322,912 to Fife; U.S. Pat. No. 6,391,275 to Fife et al.; U.S. Pat. No. 6,416,730 to Fife et al.; U.S. Pat. No. 6,527,937 to Fife; U.S. Pat. No. 6,576,099 to Kimmel, et al.; U.S. Pat. No. 6,592,740 to Fife, et al.; and U.S. Pat. No. 6,639,787 to Kimmel et al.; and U.S. Pat. No. 7,220,397 to Kimmel, et al., as well as U.S. Patent Application Publication Nos. 2005/0019581 to Schnitter; 2005/0103638 to Schnitter, et al.; 2005/0013765 to Thomas, et al.

To form the planar anode, a powder of the valve metal composition is generally employed. The powder may contain particles any of a variety of shapes, such as nodular, angular, flake, etc., as well as mixtures thereof. Particularly suitable powders are tantalum powders available from Cabot Corp. (e.g., C255 flake powder, TU4D flake/nodular powder, etc.) and H. C. Starck (e.g., NH175 nodular powder). The valve metal composition may be formed using techniques known to those skilled in the art. A precursor tantalum powder, for instance, may be formed by reducing a tantalum salt (e.g., potassium fluotantalate ($K_2TaF_7$), sodium fluotantalate ($Na_2TaF_7$), tantalum pentachloride ($TaCl_5$), etc.) with a reducing agent (e.g., hydrogen, sodium, potassium, magnesium, calcium, etc.).

Regardless of the particular method employed, the resulting powder may possess certain characteristics that enhance its ability to be formed into a capacitor anode. For example, the particles employed in the anode may be generally flat. The degree of flatness is generally defined by the "aspect ratio", i.e., the average diameter or width of the particles divided by the average thickness ("D/T"). For example, the aspect ratio of the particles may be from about 2 to about 100, in some embodiments from about 3 to about 50, in some embodiments, from about 4 to about 30. The particles may also have a specific surface area of from about 0.5 to about 10.0 $m^2/g$, in some embodiments from about 0.7 to about 5.0 $m^2/g$, and in some embodiments, from about 1.0 to about 4.0 $m^2/g$. The term "specific surface area" is defined in more detail above. The bulk density (also known as Scott density) is also typically from about 0.1 to about 2 grams per cubic centimeter ($g/cm^3$), in some embodiments from about 0.2 $g/cm^3$ to about 1.5 $g/cm^3$, and in some embodiments, from about 0.4 $g/cm^3$ to about 1 $g/cm^3$. "Bulk density" may be determined using a flow meter funnel and density cup. More specifically, the sample may be poured through the funnel into the cup until the sample completely fills and overflows the periphery of the cup, and thereafter sample may be leveled-off by a spatula, without jarring, so that it is flush with the top of the cup. The leveled sample is transferred to a balance and weighed to the nearest 0.1 gram to determine the density value. Such an apparatus is commercially available from Alcan Aluminum Corp. of Elizabeth, N.J. The particles may also have an average size (e.g., width) of from about 0.1 to about 100 micrometers, in some embodiments from about 0.5 to about 70 micrometers, and in some embodiments, from about 1 to about 50 micrometers.

To facilitate the construction of the planar anode, certain additional components may also be included in the powder. For example, the powder may be optionally mixed with a binder and/or lubricant to ensure that the particles adequately adhere to each other when pressed to form the planar anode body. Suitable binders may include, for instance, poly(vinyl butyral); poly(vinyl acetate); poly(vinyl alcohol); poly(vinyl pyrollidone); cellulosic polymers, such as carboxymethylcellulose, methyl cellulose, ethyl cellulose, hydroxyethyl cellulose, and methylhydroxyethyl cellulose; atactic polypropylene, polyethylene; polyethylene glycol (e.g., Carbowax from Dow Chemical Co.); polystyrene, poly(butadiene/styrene); polyamides, polyimides, and polyacrylamides, high molecular weight polyethers; copolymers of ethylene oxide and propylene oxide; fluoropolymers, such as polytetrafluoroethylene, polyvinylidene fluoride, and fluoro-olefin copolymers; acrylic polymers, such as sodium polyacrylate, poly(lower alkyl acrylates), poly (lower alkyl methacrylates) and copolymers of lower alkyl acrylates and methacrylates; and fatty acids and waxes, such as stearic and other soapy fatty acids, vegetable wax, microwaxes (purified paraffins), etc. The binder may be dissolved and dispersed in a solvent. Exemplary solvents may include water, alcohols, and so forth. When utilized, the percentage of binders and/or lubricants may vary from about 0.1% to about 8% by weight of the total mass. It should be understood, however, that binders and/or lubricants are not necessarily required in the present invention.

The resulting powder may be compacted to form a pellet using any conventional powder press device. For example, a press mold may be employed that is a single station compaction press containing a die and one or multiple punches. Alternatively, anvil-type compaction press molds may be used that use only a die and single lower punch. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing. The powder may be compacted around an anode lead wire. The wire may be formed from any electrically conductive material, such as tantalum, niobium, aluminum, hafnium, titanium, etc., as well as electrically conductive oxides and/or nitrides of thereof.

Any binder/lubricant may be removed after pressing by heating the pellet under vacuum at a certain temperature (e.g., from about 150° C. to about 500° C.) for several minutes. Alternatively, the binder/lubricant may also be removed by contacting the pellet with an aqueous solution, such as described in U.S. Pat. No. 6,197,252 to Bishop, et al. Thereafter, the pellet is sintered to form a porous, integral mass. The present inventors have discovered that certain sintering conditions can result in an increase in the specific charge of the resulting planar anode, as well increase in the breakdown voltage of the resulting capacitor. More particularly, the pellet is typically sintered at a temperature of from about 800° C. to about 2000° C., in some embodiments from about 1200° C. to about 1800° C., and in some embodiments, from about 1500° C. to about 1700° C., for a time of from about 5 minutes to about 100 minutes, and in some embodiments, from about 8 minutes to about 15 minutes. This may occur in one or more steps. If desired, sintering may occur in an atmosphere that limits the transfer of oxygen atoms to the planar anode. For example, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed. When employed, flake particles may be better able to withstand the high sintering temperatures and prolonged sintering times often employed in forming the planar anode, and produce a porous sintered body with low shrinkage and a large specific surface area.

Upon sintering, the pellet shrinks due to the growth of metallurgical bonds between the particles. Because shrinkage generally increases the density of the pellet, lower press densities ("green") may be employed to still achieve the desired target density. For example, the target density of the pellet after sintering is typically from about 5 to about 8 grams per cubic centimeter. As a result of the shrinking phenomenon, however, the pellet need not be pressed to such high densities, but may instead be pressed to densities of less than about 6.0 grams per cubic centimeter, and in some embodiments, from about 4.5 to about 5.5 grams per cubic centimeter. Among other things, the ability to employ lower green densities may provide significant cost savings and increase processing efficiency. It should be understood that the pressed density may not always be uniform across the pellet, particularly if compression occurs in a direction perpendicular to the longitudinal axis of the wire. Namely, the pressed density is determined by dividing the amount of material by the volume of the pressed pellet. The volume of the pellet is directly proportional to the compressed length in the direction perpendicular to the longitudinal axis of the wire. The density is inversely proportional to the compressed length. Thus, the compressed length is actually lower at those locations adjacent to the wire than the remaining locations of the pellet. The pressed density is likewise greater at those locations adjacent to the wire. For example, the density of the pellet at those locations adjacent to the wire is typically at least about 10% greater, and in some cases, at least about 20% greater than the pressed density of the pellet at the remaining locations of the pellet.

Figure 2:
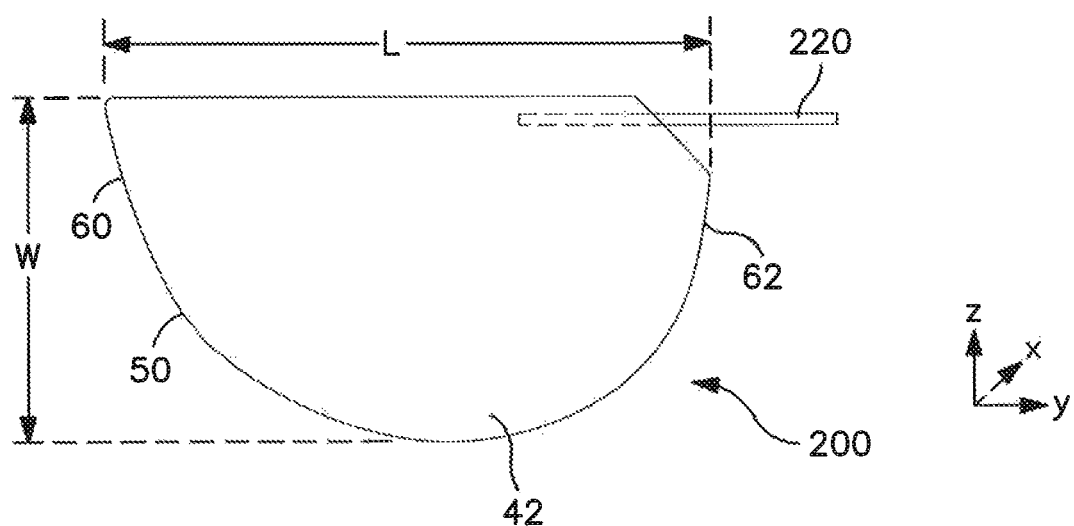
FIG. 2 is an upper surface view of an embodiment of a planar anode that may be employed in the capacitor of the present invention.
Figure 3:
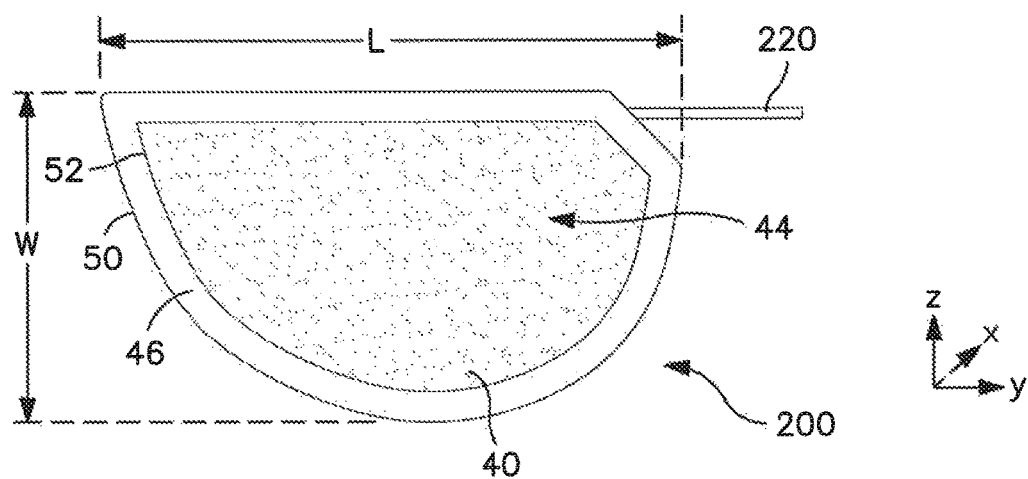
FIG. 3 is a lower surface view of an embodiment of a planar anode that may be employed in the capacitor of the present invention.

Referring to FIGS. 2-3, for example, one embodiment of a planar anode 200 is shown that contains an anode wire 220. The anode wire extends in a longitudinal direction ("y" direction) from the planar anode 200. In order to embed the anode wire 220 into the planar anode 200, a press mold may be partially filled with the powder, and then an anode wire may be inserted into the press mold. Thereafter, the mold may be filled with powder and the entire assembly compressed into a pellet.

The resulting planar anode can have a small overall thickness as compared to its overall length and overall width to improve the electrical performance and volumetric efficiency of the resulting capacitor. Referring to FIG. 2, for example, which shows an upper surface 42 of the anode 200, the length "L" represents the entire length of the anode 200 from a first end 60 to a second end 62. In certain cases, the length "L" of the anode 200 may range from about 1 to about 80 millimeters, in some embodiments from about 10 to about 60 millimeters, and in some embodiments, from about 20 to about 50 millimeters. Meanwhile, also referring to FIG. 2, the overall width "W" of the anode may also be from about 0.5 to about 60 millimeters, in some embodiments, from about 1 to about 40 millimeters, and in some embodiments, from about 5 to about 30 millimeters. Further, referring to FIGS. 4, 14, 16, and 18, typically, the overall thickness "H" of the anode is about 5 millimeters or less, in some embodiments, from about 0.05 to about 4 millimeters, in some embodiments, from about 0.1 to about 3.5 millimeters, and, in some embodiments from about 0.2 to about 2 millimeters. Generally, in some embodiments, the ratio of the overall length "L" of the anode to the overall thickness "H" of the planar anode can range from about 5 to about 50, in some embodiments from about 6 to about 40, and in some embodiments, from about 7 to about 30. Further, the ratio of the overall width "W" of the anode to the overall thickness "H" of the anode can range from about 4 to about 35, in some embodiments from about 5 to about 25, and in some embodiments, from about 6 to about 20. In addition, the thickness of the planar anode can vary across the length and/or width of the planar anode due to the presence of one or more recessed portions formed in the planar anode.

For instance, the planar anode includes at least one recessed portion on at least one of its surfaces, such as an upper surface, a lower surface, a side wall, etc. Further, the recessed portion can have any shape, such as square, rectangular, u-shaped, triangular, curved, etc. In some embodiments, the recessed portion can extend around the entire circumference or edge of the planar anode, while in other embodiments, the recessed portion can extend around only part of the circumference or edge of the planar anode. Moreover, the recessed portion can be continuously or discontinuously disposed across a surface of the planar anode. In addition, multiple recessed portions can be formed on the planar anode, where such multiple recessed portions can be present on the same surface or different surfaces of the planar anode. For instance, one or more recessed portions can be present on the upper surface, the lower surface, the side surface, or a combination thereof. Regardless of the surface in which the recessed portion is located, referring to FIGS. 4, 14, 16, and 18, the recessed portion can have a width "$W_2$" of from about 0.005 to about 30 millimeters, in some embodiments, from about 0.01 to about 20 millimeters, and in some embodiments, from about 0.1 to about 7.5 millimeters. Meanwhile, the height "$H_2$" of the recessed portion can be from about 0.005 to about 4 millimeters, in some embodiments from about 0.01 to about 3 millimeters, and in some embodiments, from about 0.05 to about 1.5 millimeters.

In addition, at least one restraint (discussed in more detail below) is positioned adjacent to and in contact with at least a part of the at least one recessed portion of the planar anode. The recessed portion of the planar anode can be shaped to generally match the shape of the restraint such that the recessed portion of the planar anode can be locked into a secure position inside the casing by the restraint. In other words, the restraint and the recessed portion of the planar anode can have complimentary geometries to allow the restraint to fit into the recessed portion in order to stabilize the anode inside the casing. Thus, the shape of the recessed portion can generally correspond with the shape of the restraint with which it is in contact. Further, while one restraint can be in continuous contact with the entire recessed portion, it should be understood that this is not required, and one or more restraints can be utilized in a discontinuous manner so that one or more restraints are spaced apart from each other in the recessed portion. As a result of the arrangement of the capacitor where the planar anode is locked into place inside the casing by a restraint that fits into a recessed portion of the planar anode, the restraint can stabilize the anode when the capacitor is subjected to high levels of shock or vibration without increasing the overall dimensions of the capacitor.

Figure 4:
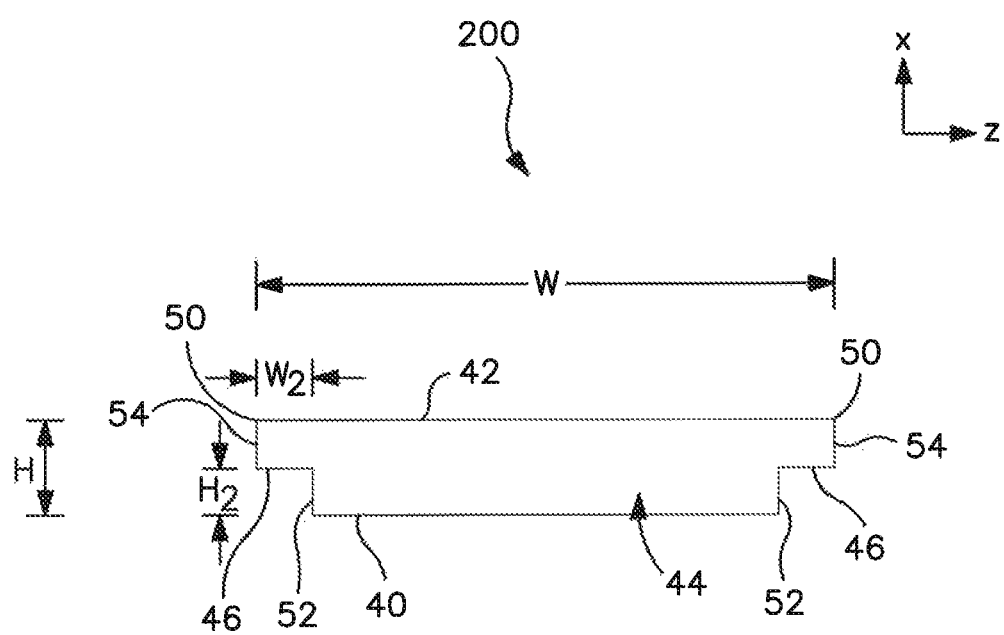
FIG. 4 is a cross-sectional view of the planar anode of FIGS. 2 and 3 across its width.
Figure 5:
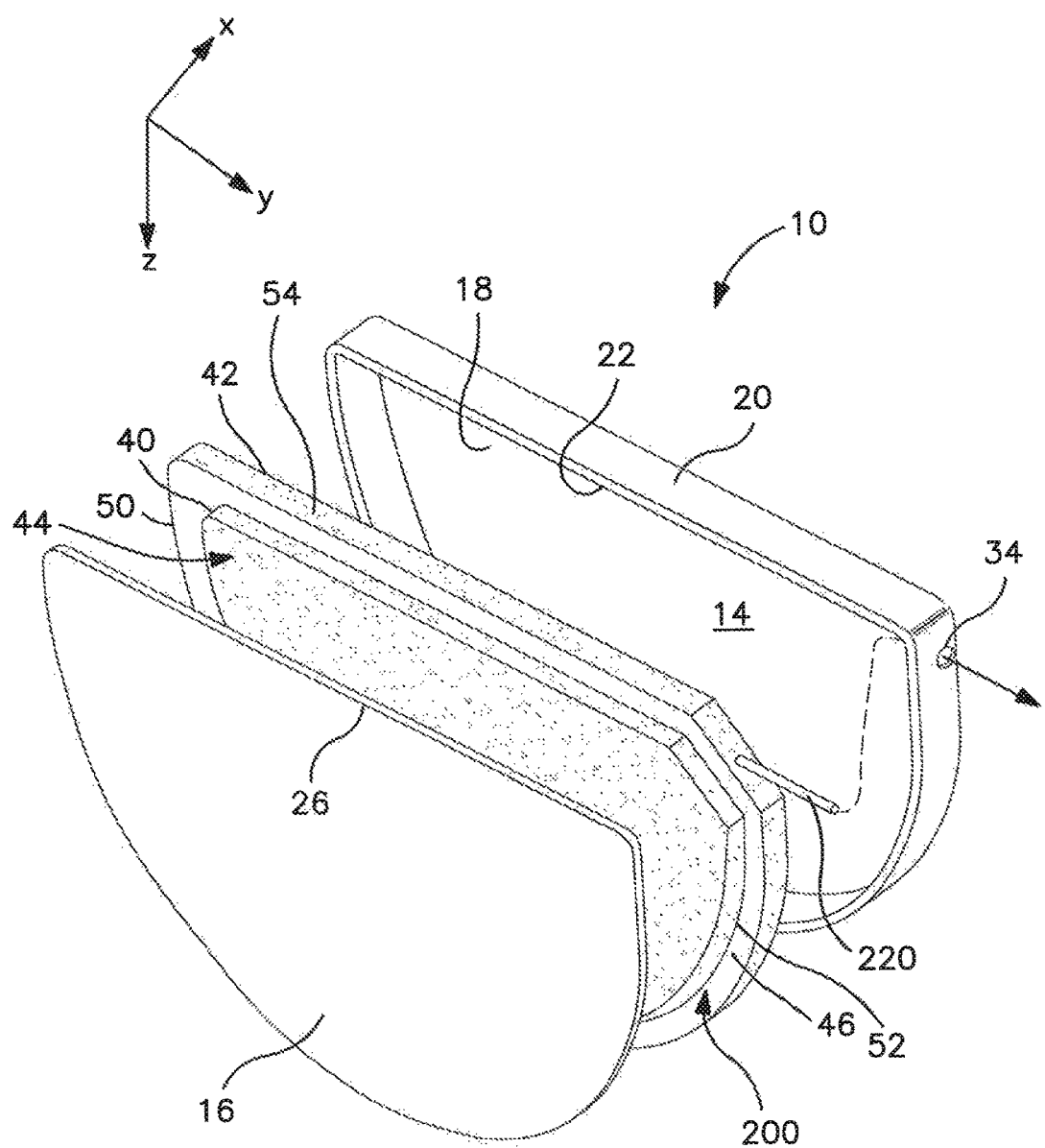
FIG. 5 is an exploded perspective view illustrating the planar anode of FIGS. 2 and 3 surrounded by a casing to form the capacitor shown in FIG. 1 without one or more restraints shown.
Figure 12:
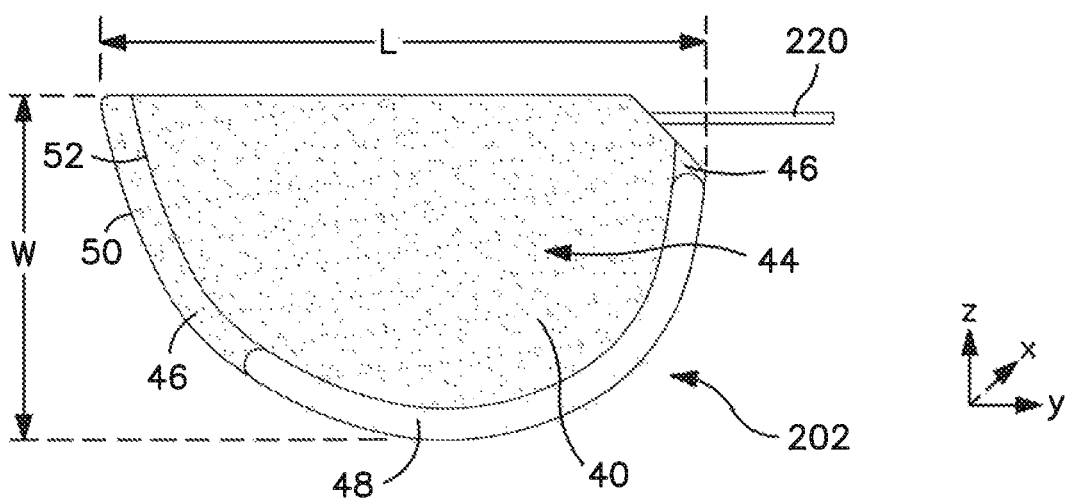
FIG. 12 is a lower surface view of another embodiment of a planar anode and the corresponding restraints that may be employed in the capacitor of the present invention.
Figure 13:
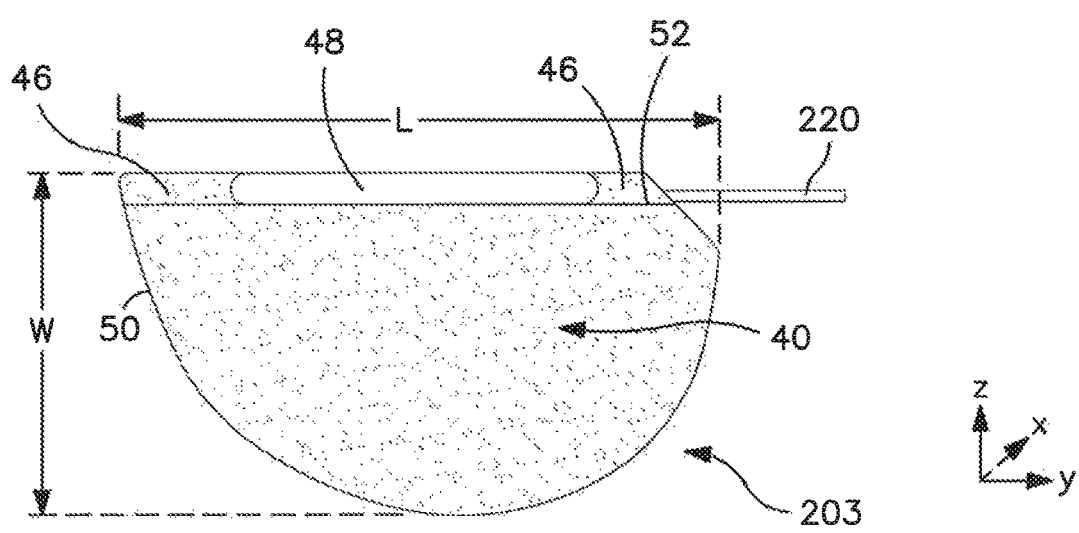
FIG. 13 is a lower surface view of another embodiment of a planar anode and the corresponding restraints that may be employed in the capacitor of the present invention.
Figure 14:
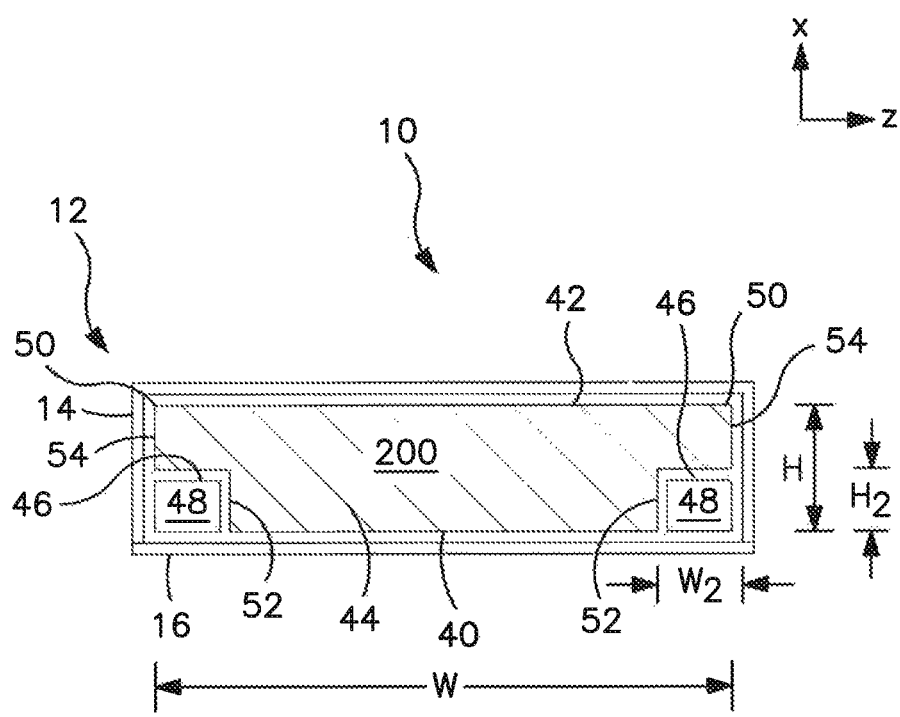
FIG. 14 is a cross-sectional view of the capacitor of FIG. 6 across its width.

Turning first to the planar anode of FIGS. 3-14, and as shown specifically in FIGS. 4, 5, and 14, a portion of the planar anode 200 has a thickness "H" and a portion of the anode has a reduced thickness of "H" minus "H2," where, as discussed above, "H2" refers to the height or thickness of a recessed portion 46 of the planar anode 200 formed in the side wall 54 of the planar anode 200. As shown in FIGS. 3-14, the recessed portion 46 of the anode is formed in the lower surface 40 of the planar anode 200 at the side wall 54, and specifically around the periphery of the planar anode 200 between a circumferential edge 50 of the planar anode 200 and a circumferential edge 52 of a protruding central portion 44 of the planar anode 200. In this regard, the planar anode 200 can be described as having a stepped or flanged shape, where the central portion has a larger thickness than the thickness of the periphery of the planar anode. The variance in thickness at the lower surface 40 of the planar anode 200 between the recessed portion 46 and the central protruding portion 44 can be accomplished during formation of the planar anode based on the shape of the press mold used to form the planar anode 200, or the resulting anode pellet can be modified after molding to vary the thickness across the length and/or width of the planar anode. Further, it is to be understood that although FIGS. 3-14 show formation of the recessed portion 46 in the lower surface 40 of the planar anode, this is not required, and, instead, the recessed portion 46 can be formed in an upper surface of the anode, a sidewall of the anode, etc. Further, multiple recessed portions can be formed in one or more surfaces of the planar anode. Various planar anodes encompassed by the present invention are discussed in detail below.

In FIGS. 3-14, the thickness variance as a result of the recessed portion 46 results in a planar anode 200 having a protruding central portion 44 and a recessed portion 46 at a periphery of the lower surface 40, as shown in FIGS. 3 and 5. Further, as shown in FIGS. 3-11, the recessed portion 46 can extend around the planar anode 200 from a circumferential inner edge 52 of the protruding central portion 44 to an overall circumferential outer edge 50 of the planar anode 200. Generally, when the recessed portion 46 is formed in a lower surface 40 of the planar anode 200, the protruding central portion 44 can have a surface area that is from about 50% to about 99.5% of the surface area of the upper surface 42 of the planar anode 200 defined by the circumferential outer edge 50, regardless of the particular geometry of the protruding central portion 44 as determined by the circumferential inner edge 52. In another embodiment, the protruding central portion 44 can have a surface area that is from about 60% to about 99% of the surface area of the upper surface 42 of the planar anode 200. Meanwhile, in still another embodiment, the protruding central portion 44 can have a surface area that is from about 70% to about 98% of the surface area of the upper surface 42 of the planar anode 200. Likewise, the recessed portion 46 located about the periphery of the planar anode 200 can have a surface area that is from about 0.5% to about 50% of the surface area of the upper surface 42 of the anode 200, regardless of the particular geometry of the recessed portion 46 as determined by the circumferential outer edge 50 of the planar anode 200 and the circumferential inner edge 52 of the protruding central portion 44. In another embodiment, the recessed portion 46 can have a surface area that is from about 1% to about 40% of the surface area of the upper surface 42 of the planar anode 200. Meanwhile, in still another embodiment, the recessed portion 46 can have a surface area that is from about 2% to about 30% of the surface area of the upper surface 42 of the planar anode 200. Further, it is to be understand that the same surface area ranges can apply when the recessed portion 46 is formed in an upper surface 42 of the planar anode 200 such that the lower surface 40 of the planar anode 200 does not included a recessed portion.

As shown in FIGS. 3 and 5, the circumferential inner edge 52 of the protruding central portion 44 of the planar anode 200 can have generally the same shape, albeit on a smaller scale, as the circumferential outer edge 50 of the anode 200. Although shown as a "D-shape" in FIGS. 2-3 and 5-11, it should also be understood that the planar anode 200 and the protruding central portion 44 may possess any other desired shape, such as square, rectangular, circular, oval, triangular, etc. Further, the overall planar anode shape can include polygonal shapes having more than four (4) edges (e.g., hexagon, octagon, heptagon, pentagon, etc.), which may be desired due to their relatively high surface area.

Figure 11:
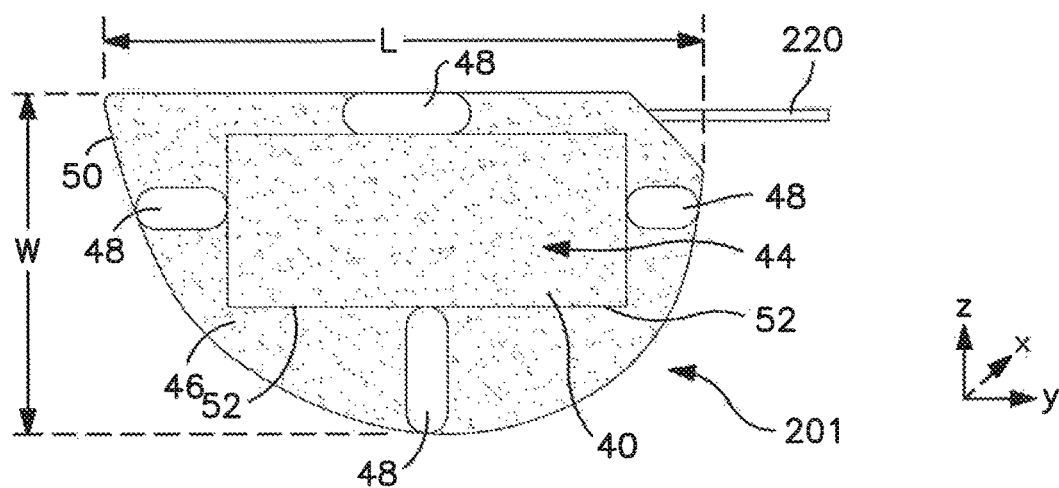
FIG. 11 is a lower surface view of yet another embodiment of a planar anode and the corresponding restraints that may be employed in the capacitor of the present invention.

For instance, in FIGS. 3 and 5, both the larger circumferential outer edge 50 of the overall planar anode 200 and the smaller circumferential inner edge 52 of the protruding central portion 44 of the planar anode 200 are generally D-shaped. However, it is to be understood that the overall planar anode 200 can be any shape, and that the protruding central portion 44 can be any shape, and it is not required that the protruding central portion 44 have a shape that is the same as that of the overall shape of the planar anode 200. For example, as shown in FIG. 11, the protruding central portion 44 can be rectangular-shaped as defined by its circumferential inner edge 52, while the overall planar anode 201 can be D-shaped as defined by its circumferential outer edge 50, or vice versa (not shown).

Further, it is also to be understood that it is not required that the recessed portion 46 extend completely or entirely around a surface of the planar anode as is shown in FIGS. 3-11 for the planar anodes 200 and 201, and other recessed portion geometries are also contemplated. For example, the planar anode 202 of FIG. 12 is D-shaped but includes a recessed portion 46 that is formed in the lower surface 40 of the planar anode 202 so that it extends around the curved portion of the circumferential edge 50 of the planar anode 202 and does not extend along the straight edge of its length "L." On the other hand, the planar anode 203 of FIG. 13 is D-shaped but includes a recessed portion 46 that extends only along the straight edge of its length "L" and does not extend along its curved portion of the circumferential edge 50 of the planar anode 203.

Figure 15:
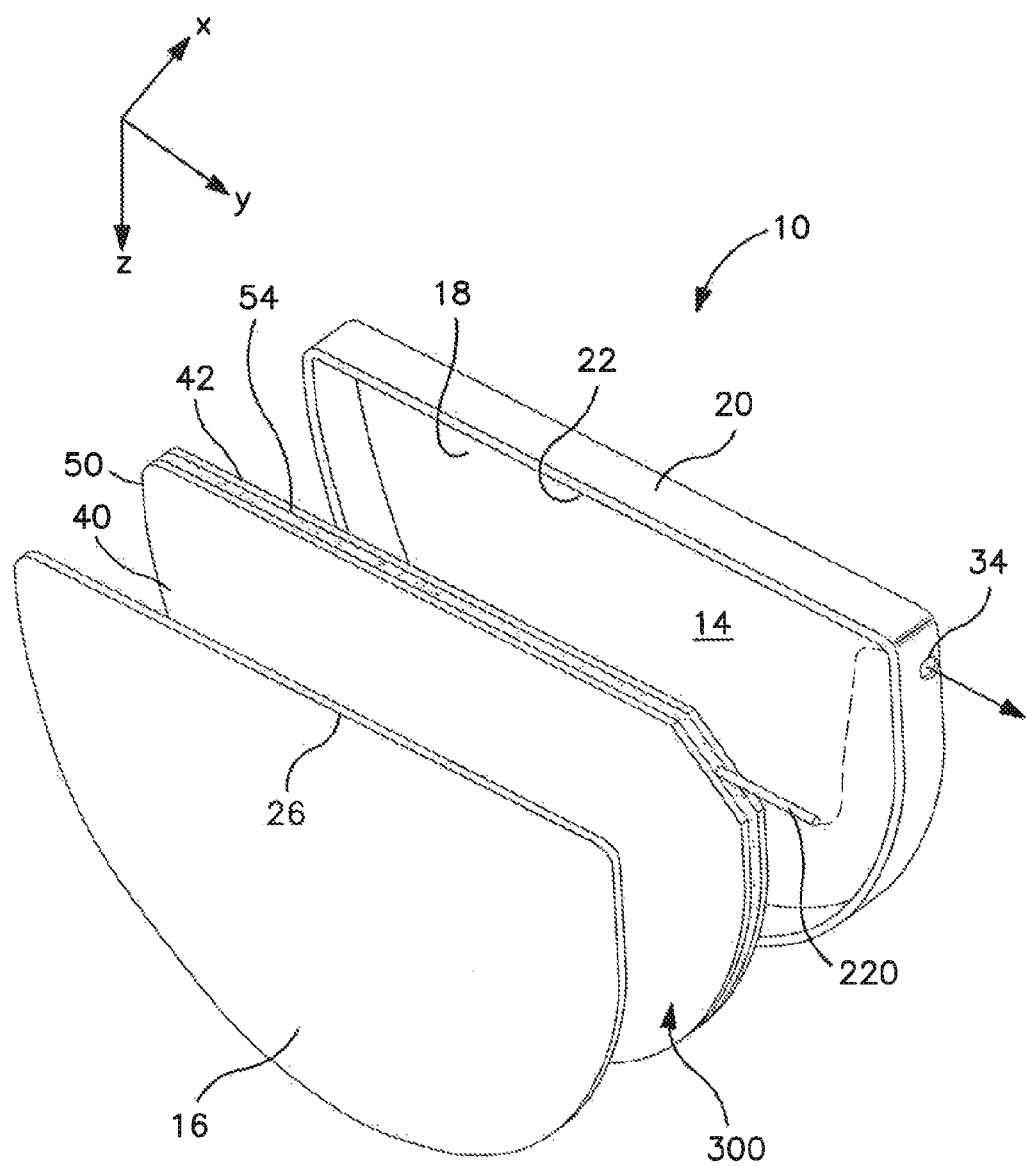
FIG. 15 is an exploded perspective view illustrating another embodiment of a planar anode surrounded by a casing to form the capacitor shown in FIG. 1 without one or more restraints shown.
Figure 16:
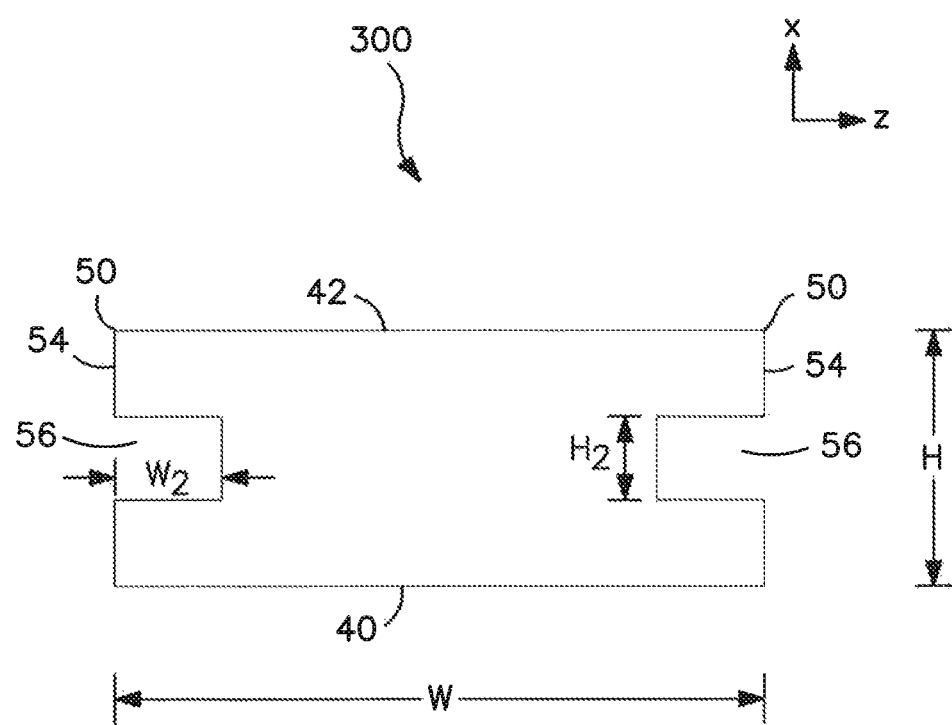
FIG. 16 is a cross-sectional view of the planar anode of FIG. 15 across its width.

Turning now to FIGS. 15-18, an additional embodiment of a planar anode 300 is shown where the recessed portion 56 is formed in a side wall 54 of the planar anode 300 at a different location than that of FIGS. 3-14. As shown in FIGS. 15 and 16, for example, the recessed portion 56 can extend around the entire circumferential edge 50 of the anode 300 but can be formed in the middle of the side wall 54 or along any other portion of the side wall 54 besides the upper surface 42 or the lower surface 40. In other words, the upper surface 42 and the lower surface 40 of the planar anode 300 can have the same dimensions while the recessed portion 56 can be disposed between the upper surface 42 and the lower surface 40 at some location in the side wall 54.

Generally, the aforementioned recessed portions 46 or 56 permit the use of one or more restraints 48 to hold the planar anode 200, 201, 202, 203, or 300 in place inside the casing 12 without having to increase one or more dimensions of the casing 12, which is, as discussed above, important to minimize the space occupied implantable medical devices incorporating the capacitor 10 of the present invention. Various embodiments of one or more restraints 48 which can be used in connection with the recessed portions 46 and 56 of the anodes described above are shown in FIGS. 6-14 and 17-18 and discussed in more detail below.

In other embodiments, however, it is to be understood that the restraint may contact more than just the recessed portions of the anodes contemplated by the present invention. Turning now to FIGS. 19-23, two additional restraint and anode configurations are shown.

Figure 19:
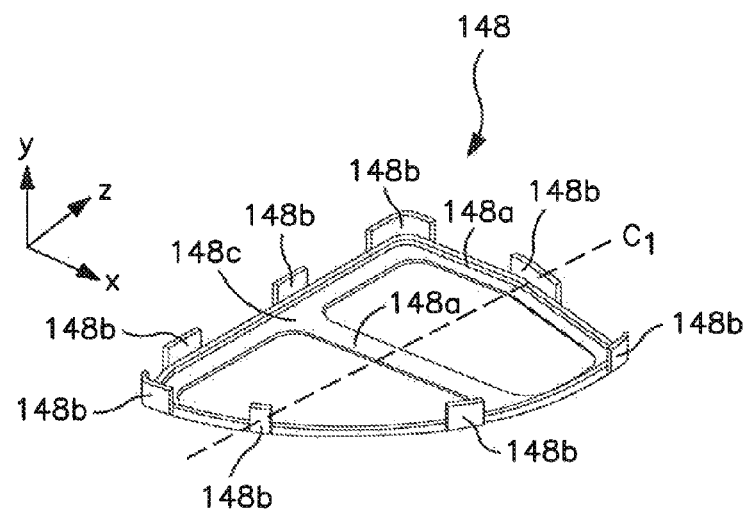
FIG. 19 is a perspective view of a restraint that may be employed in the capacitor of the present invention.
Figure 20:
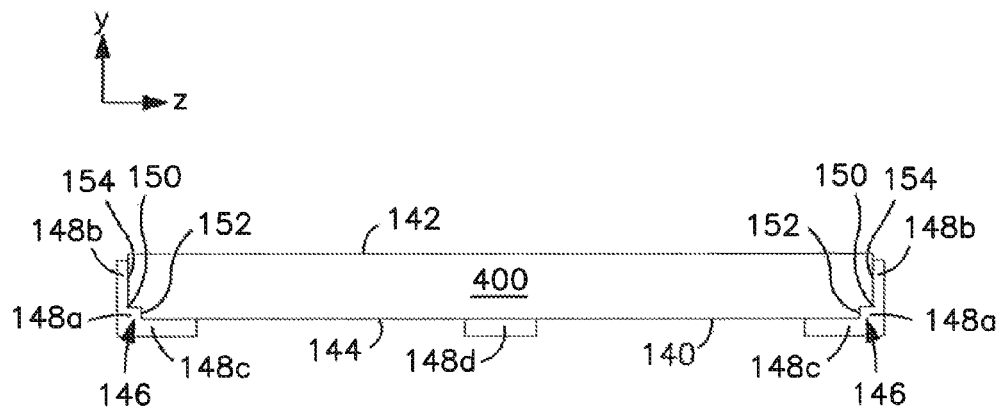
FIG. 20 is a cross-sectional view of the restraint of FIG. 19 at line $C_1$, where a planar anode has been inserted into the restraint.
Figure 21:
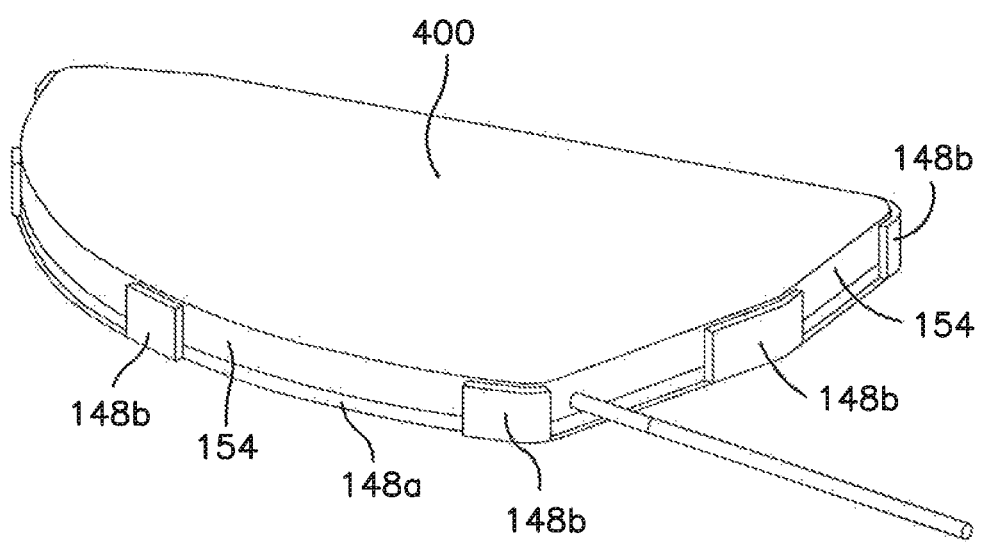
FIG. 21 is a perspective view of the planar anode/restraint configuration of FIG. 20.

FIG. 19 is a perspective view of one embodiment of a restraint 148 that may be employed in the capacitor of the present invention. The restraint is in the form of a nest or cage that can hold a planar anode, as shown in FIG. 20, which is a cross-sectional view of the restraint of FIG. 19 at line $C_1$, where a planar anode 400 has been inserted into the restraint 148. Meanwhile, FIG. 21 is a perspective view of the planar anode 400/restraint 148 configuration of FIG. 20. As shown in FIGS. 19-21, the restraint 148 can have a portion 148a that is shaped to generally match the recessed portion 146 of the anode 400 formed at the circumferential edge 152 of the protruding central portion 144 of the anode 400. Thus, the portion 148a of the restraint can fit into the recessed portion 146 of the anode 400 to lock the anode 400 into a secure and stable position. Meanwhile, multiple tab portions 148b of the restraint 148 can extend around the circumference of the restraint 148, and the tab portions extend in the y-direction or thickness/height direction of the anode 400 and contact the sidewall 154 of the anode 400 formed by the circumferential edge 150 of the anode 400 to further secure and stabilize the anode 400 by providing additional points of contact between the restraint 148 and the anode 400. In addition, a portion of the restraint 148c can extend around the circumference and contact the lower surface 140 of the anode to provide even further stabilization to the anode. Further, a portion of the restraint 148d can extend across the lower surface 140 of the anode at a generally centralized location to provide additional contact between the restraint 148 and the protruding central portion 144 of the anode 400 for additional stabilization.

Figure 22:
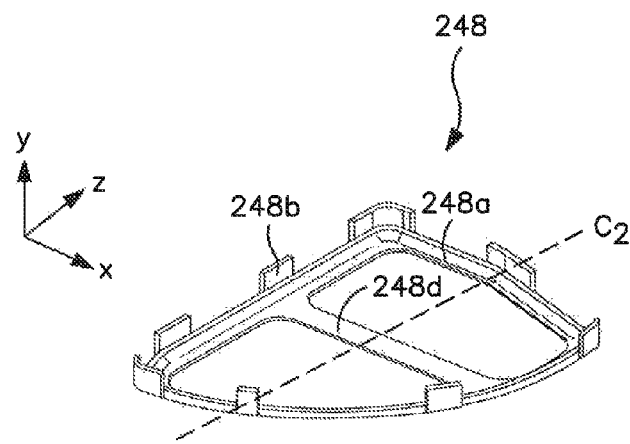
FIG. 22 is a perspective view of another restraint that may be employed in the capacitor of the present invention.
Figure 23:
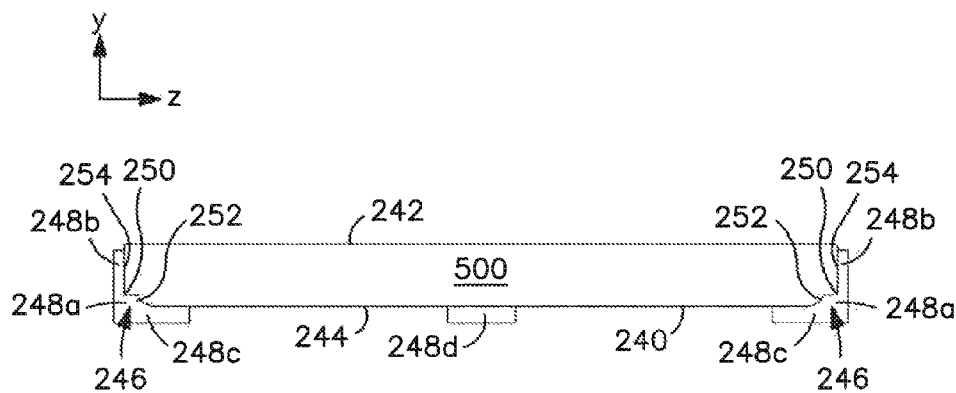
FIG. 23 is a cross-sectional view of the restraint of FIG. 22 at line $C_2$, where a planar anode has been inserted into the restraint.

FIG. 22 is a perspective view of another restraint that may be employed in the capacitor of the present invention. The restraint is in the form of a nest or cage that can hold a planar anode, as shown in FIG. 23, which is a cross-sectional view of the restraint of FIG. 22 at line $C_2$, where a planar anode 500 has been inserted into the restraint 248. As shown in FIGS. 22-23, the restraint 248 can have a portion 248a that is shaped to generally match the recessed portion 246 of the anode 500 formed at the circumferential edge 252 of the protruding central portion 244 of the anode 500, which is similar to the shape of anode 400 from FIGS. 20-21 except that the circumferential edge 252 has a curved geometry rather than forming an approximately 90° angle like the circumferential edge 152 of the anode 400 shown in FIG. 20. Thus, the portion 248a of the restraint can fit into the recessed portion 246 of the anode 500 to lock the anode 500 into a secure and stable position. Meanwhile, multiple tab portions 248b of the restraint 248 can extend around the circumference of the restraint 248, and the tab portions extend in the y-direction or thickness/height direction of the anode 500 and contact the sidewall 254 of the anode 500 formed at the circumferential edge 250 of the anode 500 to further secure and stabilize the anode 500 by providing additional points of contact between the restraint 248 and the anode 500. In addition, a portion of the restraint 248c can extend around the circumference and contact the lower surface 240 of the anode to provide even further stabilization to the anode. Further, a portion of the restraint 248d can extend across the lower surface 240 of the anode at a generally centralized location to provide additional contact between the restraint 248 and the protruding central portion 244 of the anode 500 for additional stabilization.

As shown in FIGS. 20-21 and 23, the restraints for anode 400 and anode 500 can be positioned adjacent to and in contact the recessed portion of the anode, as well at least a portion of the lower surface of the anode and at least a portion of the circumferential edge of the anode. The recessed portion of the planar anode can be shaped to generally match the shape of the restraint such that the recessed portion of the planar anode can be locked into a secure position inside the casing by the restraint. In other words, the restraint and the recessed portion of the planar anode can have complimentary geometries to allow the restraint to fit into the recessed portion in order to stabilize the planar anode inside the casing. Thus, the shape of the recessed portion can generally correspond with the shape of the restraint with which it is in contact. As shown in FIGS. 20-21 and 23, the restraint can be in continuous contact with the entire recessed portion. Similar to the restraints of FIGS. 6-12, 14-15, and 17-18, as a result of the arrangement of the capacitor where the planar anode is locked into place inside the casing by a restraint that fits into a recessed portion of the planar anode, the restraint can stabilize the planar anode when the capacitor is subjected to high levels of shock or vibration without increasing the overall dimensions of the capacitor. In addition, to further enhance the stability of the anode, as shown and as discussed above, the restraint of FIGS. 19-21 and the restraint of FIG. 22-23 can form a nest or cage for the anode in that it can also include components that are in contact with a portion of the lower surface of the anode and a portion of the circumferential edge or sidewall of the anode, which can further help the restraint to lock the anode in place.

Regardless of the particular arrangement or process by which the planar anode 200, 201, 202, 203, 300, 400, or 500 can be configured to have a recessed portion 46 at its lower surface 40 or any other suitable surface (e.g., upper surface, side wall, etc.), as stated above, the overall thickness of the anode 200, 201, 202, 203, 300, 400, or 500 is generally small to improve the electrical performance and volumetric efficiency of the resulting capacitor.

Moreover, regardless of the particular geometry of the planar anode, the planar anode also contains a dielectric formed by anodically oxidizing ("anodizing") the sintered anode so that a dielectric layer is formed over and/or within the planar anode. For example, a tantalum (Ta) anode may be anodized to tantalum pentoxide ($Ta_2O_5$). Typically, anodization is performed by initially applying a solution to the anode, such as by dipping anode into the electrolyte. Aqueous solvents (e.g., water) and/or non-aqueous solvents (e.g., ethylene glycol) may be employed. To enhance conductivity, a compound may be employed that is capable of dissociating in the solvent to form ions. Examples of such compounds include, for instance, acids, such as described below with respect to the electrolyte. For example, an acid (e.g., phosphoric acid) may constitute from about 0.01 wt. % to about 5 wt. %, in some embodiments from about 0.05 wt. % to about 0.8 wt. %, and in some embodiments, from about 0.1 wt. % to about 0.5 wt. % of the anodizing solution. If desired, blends of acids may also be employed.

A current is passed through the anodizing solution to form the dielectric layer. The value of the formation voltage manages the thickness of the dielectric layer. For example, the power supply may be initially set up at a galvanostatic mode until the required voltage is reached. Thereafter, the power supply may be switched to a potentiostatic mode to ensure that the desired dielectric thickness is formed over the entire surface of the anode. Of course, other known methods may also be employed, such as pulse or step potentiostatic methods. The temperature of the anodizing solution may range from about 10° C. to about 200° C., in some embodiments from about 20° C. to about 150° C., and in some embodiments, from about 30° C. to about 100° C. The resulting dielectric layer may be formed on a surface of the anode and within its pores. When employed, the specific nature of the powder may allow the resulting anode to achieve a high specific charge even at the high formation voltages often employed in the present invention. For example, within the ranges rioted above, the anode may still be able to a specific charge of from about 2,000 µF*V/g to about 20,000 µF*V/g, in some embodiments from about 5,000 µF*V/g to about 15,000 µF*V/g or more, and in some embodiments, from about 8,000 to about 12,000 µF*V/g.

II. Cathode

In addition to the anode, a cathode is also employed in the capacitor that may be constructed using any of a variety of techniques. In one embodiment, the cathode contains a metal substrate, which may include any metal, such as tantalum, niobium, aluminum, nickel, hafnium, titanium, copper, silver, steel (e.g., stainless), alloys thereof (e.g., electrically conductive oxides), composites thereof (e.g., metal coated with electrically conductive oxide), and so forth, that is coated with an electrochemically-active material. Titanium and tantalum, as well as alloys thereof, are particularly suitable for use in the present invention. The geometric configuration of the substrate may generally vary as is well known to those skilled in the art, such as in the form of a container, can, foil, sheet, screen, mesh, etc. Although not required, in one embodiment, for example, the metal substrate can form the capacitor casing in which the planar anode is disposed, and such casing can have a D-shape or any other shape that generally corresponds to the shape of the planar anode. For instance, it should be understood that any geometric configuration may be employed in the present invention, such as cylindrical, rectangular, triangular, prismatic, etc.

The substrate may be roughened to increase its surface area and increase the degree to which an electrochemically-active material may be able to adhere thereto. In one embodiment, for example, the surface is chemically etched, such as by applying a solution of a corrosive substance (e.g., hydrochloric acid) to the surface. The surface may also be electrochemically etched, such as by applying a voltage to a solution of the corrosive substance so that it undergoes electrolysis. The voltage may be raised to a sufficiently high level to initiate "sparking" at the surface of the substrate, which is believed to create high local surface temperatures sufficient that etches away the substrate. This technique is described in more detail in U.S. Pat. No. 8,279,585 to Dreissig, et al., which is incorporated herein in its entirety by reference thereto for all purposes. In addition to chemical or electrochemical roughening techniques, mechanical roughening may also be employed. In one embodiment, for instance, the surface of the metal substrate may be abrasive blasted by propelling a stream of abrasive media (e.g., sand) against at least a portion of a surface thereof.

An electrochemically-active material may also be applied to the cathode substrate to inhibit corrosion and also act as a heat barrier when voltage is increased. The electrochemically-active material may be formed from one or more layers. The material employed in such layer(s) may vary. Any of a variety of known electrochemically-active materials may generally be employed. One suitable material is a conductive polymer, such as those that are π-conjugated and have electrical conductivity after oxidation or reduction (e.g., electrical conductivity of at least about 1 µS cm$^{-1}$ after oxidation). Examples of such π-conjugated conductive polymers include, for instance, polyheterocycles (e.g., polypyrroles, polythiophenes, polyanilines, etc.), polyacetylenes, poly-p-phenylenes, polyphenolates, and so forth.

Substituted polythiophenes are particularly suitable for use as conductive polymer in that they have particularly good mechanical robustness and electrical performance. Without intending to be limited by theory, it is believed that charging of the capacitor to a high voltage (e.g., greater than the formation voltage) forces ions of the electrolyte into coatings containing such substituted polythiophenes. This causes the conductive polymer to "swell" and retain the ions near the surface, thereby enhancing charge density. Because the polymer is generally amorphous and non-crystalline, it can also dissipate and/or absorb the heat associated with the high voltage. Upon discharge, it is also believed that the substituted polythiophene "relaxes" and allows ions in the electrolyte to move out of the coating. Through such swelling and relaxation mechanism, charge density near the metal substrate can be increased without a chemical reaction with the electrolyte. Accordingly, mechanical robustness and good electrical performance may be provided without the need for conventional conductive coatings, such as those made from activated carbon or metal oxides (e.g., ruthenium oxide). In fact, excellent results may be achieved using the coating as the principal material on the metal substrate. That is, the coating may constitute at least about 90 wt. %, in some embodiments at least about 92 wt. %, and in some embodiments, at least about 95 wt. % of the material(s) present on the metal substrate. Nevertheless, it should be understood that other conductive coatings may also be used in some embodiments of the present invention.

In one particular embodiment, the substituted polythiophene has the following general structure:

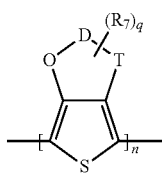

wherein,

T is O or S;

D is an optionally substituted $C_1$ to $C_5$ alkylene radical (e.g., methylene, ethylene, n-propylene, n-butylene, n-pentylene, etc.);

$R_7$ is a linear or branched, optionally substituted $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.); optionally substituted $C_5$ to $C_{12}$ cycloalkyl radical (e.g., cyclopentyl, cyclohexyl, cycloheptyl, cyclooctyl, cyclononyl cyclodecyl, etc.); optionally substituted $C_6$ to $C_{14}$ aryl radical (e.g., phenyl, naphthyl, etc.); optionally substituted $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); optionally substituted $C_1$ to $C_4$ hydroxyalkyl radical, or hydroxyl radical; and q is an integer from 0 to 8, in some embodiments, from 0 to 2, and in one embodiment, 0; and n is from 2 to 5,000, in some embodiments from 4 to 2,000, and in some embodiments, from 5 to 1,000. Example of substituents for the radicals "0" or "$R_7$" include, for instance, alkyl, cycloalkyl, aryl, aralkyl, alkoxy, halogen, ether, thioether, disulphide, sulfoxide, sulfone, sulfonate, amino, aldehyde, keto, carboxylic acid ester, carboxylic acid, carbonate, carboxylate, cyano, alkylsilane and alkoxysilane groups, carboxylamide groups, and so forth.

Particularly suitable thiophene polymers are those in which "D" is an optionally substituted $C_2$ to $C_3$ alkylene radical. For instance, the polymer may be optionally substituted poly(3,4-ethylenedioxythiophene), which has the following general structure:

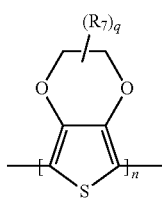

Methods for forming conductive polymers, such as described above, are well known in the art. For instance, U.S. Pat. No. 6,987,663 to Merker, et al, describes various techniques for forming substituted polythiophenes from a monomeric precursor. The monomeric precursor may, for instance, have the following structure:

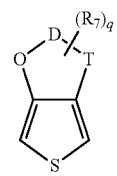

wherein,

T, D, $R_7$, and q are defined above. Particularly suitable thiophene monomers are those in which "D" is an optionally substituted $C_2$ to $C_3$ alkylene radical. For instance, optionally substituted 3,4-alkylenedioxythiophenes may be employed that have the general structure:

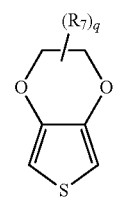

wherein, $R_7$ and q are as defined above. In one particular embodiment, "q" is 0. One commercially suitable example of 3,4-ethylenedioxythiophene is available from Heraeus Clevios under the designation Clevios™ M. Other suitable monomers are also described in U.S. Pat. No. 5,111,327 to Blohm, et al. and U.S. Pat. No. 6,635,729 to Groenendaal, et al. Derivatives of these monomers may also be employed that are, for example, dimers or trimers of the above monomers. Higher molecular derivatives, i.e., tetramers, pentamers, etc. of the monomers are suitable for use in the present invention. The derivatives may be made up of identical or different monomer units and used in pure form and in a mixture with one another and/or with the monomers. Oxidized or reduced forms of these precursors may also be employed.

The thiophene monomers may be chemically polymerized in the presence of an oxidative catalyst. The oxidative catalyst typically includes a transition metal cation, such as iron(III), copper(II), chromium(VI), cerium(IV), manganese (IV), manganese(VII), ruthenium(III) cations, etc. A dopant may also be employed to provide excess charge to the conductive polymer and stabilize the conductivity of the polymer. The dopant typically includes an inorganic or organic anion, such as an ion of a sulfonic acid. In certain embodiments, the oxidative catalyst employed in the precursor solution has both a catalytic and doping functionality in that it includes a cation (e.g., transition metal) and anion (e.g., sulfonic acid). For example, the oxidative catalyst may be a transition metal salt that includes iron(III) cations, such as iron(III) halides (e.g., $FeCl_3$) or iron(III) salts of other inorganic acids, such as $Fe(ClO_4)_3$ or $Fe_2(SO_4)_3$ and the iron(III) salts of organic acids and inorganic acids comprising organic radicals. Examples of iron (III) salts of inorganic acids with organic radicals include, for instance, iron(III)

salts of sulfuric acid monoesters of $C_1$ to $C_{20}$ alkanols (e.g., iron(III) salt of lauryl sulfate). Likewise, examples of iron (III) salts of organic acids include, for instance, iron(III) salts of $C_1$ to $C_{20}$ alkane sulfonic acids (e.g., methane, ethane, propane, butane, or dodecane sulfonic acid); iron (III) salts of aliphatic perfluorosulfonic acids (e.g., trifluoromethane sulfonic acid, perfluorobutane sulfonic acid, or perfluorooctane sulfonic acid); iron (III) salts of aliphatic $C_1$ to $C_{20}$ carboxylic acids (e.g., 2-ethylhexylcarboxylic acid); iron (III) salts of aliphatic perfluorocarboxylic acids (e.g., trifluoroacetic acid or perfluorooctane acid); iron (III) salts of aromatic sulfonic acids optionally substituted by $C_1$ to $C_{20}$ alkyl groups (e.g., benzene sulfonic acid, o-toluene sulfonic acid, p-toluene sulfonic acid, or dodecylbenzene sulfonic acid); iron (III) salts of cycloalkane sulfonic acids (e.g., camphor sulfonic acid); and so forth. Mixtures of these above-mentioned iron(III) salts may also be used. Iron(III)-p-toluene sulfonate, iron(III)-o-toluene sulfonate, and mixtures thereof, are particularly suitable. One commercially suitable example of iron(III)-p-toluene sulfonate is available from Heraeus Clevios under the designation Clevios™ C.

Various methods may be utilized to form a conductive polymer layer. In one embodiment, the oxidative catalyst and monomer are applied, either sequentially or together, such that the polymerization reaction occurs in situ on the substrate. Suitable application techniques may include screen-printing, dipping, electrophoretic coating, and spraying, may be used to form a conductive polymer coating. As an example, the monomer may initially be mixed with the oxidative catalyst to form a precursor solution. Once the mixture is formed, it may be applied to the substrate and then allowed to polymerize so that the conductive coating is formed on the surface. Alternatively, the oxidative catalyst and monomer may be applied sequentially. In one embodiment, for example, the oxidative catalyst is dissolved in an organic solvent (e.g., butanol) and then applied as a dipping solution. The substrate may then be dried to remove the solvent therefrom. Thereafter, the substrate may be dipped into a solution containing the monomer. Polymerization is typically performed at temperatures of from about −10° C. to about 250° C., and in some embodiments, from about 0° C. to about 200° C., depending on the oxidizing agent used and desired reaction time. Suitable polymerization techniques, such as described above, may be described in more detail in U.S. Pat. No. 7,515,396 to Biler. Still other methods for applying such conductive coating(s) may be described in U.S. Pat. No. 5,457,862 to Sakata, et al., U.S. Pat. No. 5,473,503 to Sakata, et al., U.S. Pat. No. 5,729,428 to Sakata, et al., and U.S. Pat. No. 5,812,367 to Kudoh, et al.

In addition to in situ application, a conductive polymer layer may also be applied in the form of a dispersion of conductive polymer particles. Although their size may vary, it is typically desired that the particles possess a small diameter to increase the surface area available for adhering to the substrate. For example, the particles may have an average diameter of from about 1 to about 500 nanometers, in some embodiments from about 5 to about 400 nanometers, and in some embodiments, from about 10 to about 300 nanometers. The $D_{90}$ value of the particles (particles having a diameter of less than or equal to the $D_{90}$ value constitute 90% of the total volume of all of the solid particles) may be about 15 micrometers or less, in some embodiments about 10 micrometers or less, and in some embodiments, from about 1 nanometer to about 8 micrometers. The diameter of the particles may be determined using known techniques, such as by ultracentrifuge, laser diffraction, etc.

If desired, one or more of the above-described application steps may be repeated until the desired thickness of the coating is achieved. In some embodiments, only a relatively thin layer of the coating is formed at a time. The total target thickness of the coating may generally vary depending on the desired properties of the capacitor. Typically, the resulting conductive polymer coating has a thickness of from about 0.2 micrometers ("μm") to about 50 μm, in some embodiments from about 0.5 μm to about 20 μm, and in some embodiments, from about 1 μm to about 5 μm. It should be understood that the thickness of the coating is not necessarily the same at all locations on the substrate. Nevertheless, the average thickness of the coating on the substrate generally falls within the ranges noted above.

The conductive polymer layer may optionally be healed. Healing may occur after each application of a conductive polymer layer or may occur after the application of the entire coating. In some embodiments, the conductive polymer can be healed by dipping the part into an electrolyte solution, and thereafter applying a constant voltage to the solution until the current is reduced to a preselected level. If desired, such healing can be accomplished in multiple steps. For example, an electrolyte solution can be a dilute solution of the monomer, the catalyst, and dopant in an alcohol solvent (e.g., ethanol). The coating may also be washed if desired to remove various byproducts, excess reagents, and so forth.

III. Restraint

In addition to a planar anode and a cathode, the capacitor of the present invention includes a restraint. The restraint employed in the capacitor assembly of the present invention is configured to lock the planar anode in place and prevent the planar anode from moving when the capacitor element is subjected to vibrational forces. In this regard, the restraint typically possesses a certain degree of strength that allows it to retain the capacitor element in a relatively fixed positioned even when it is subjected to vibrational forces, yet is not so strong that it cracks. For example, the restraint may possess a tensile strength of from about 1 to about 150 Megapascals ("MPa"), in some embodiments from about 2 to about 100 MPa, in some embodiments from about 10 to about 80 MPa, and in some embodiments, from about 20 to about 70 MPa, measured at a temperature of about 25° C. It is normally desired that the restraint is not electrically conductive.

Although any of a variety of materials may be employed that have the desired strength properties noted above, particularly suitable materials include for instance, polymers, glass, and ceramics. For instance, when the restraint is a polymeric restraint, the restraint can include a polyolefin (e.g., polypropylene, polyethylene, etc.), a fluoropolymer (e.g., polytetrafluoroetheylene), a curable thermosetting resin (e.g., an epoxy resin, a polyimide, a melamine resin, an urea-formaldehyde resin, polyurethane, a silicone polymer, a phenolic resin, etc.).

The particular manner in which the aforementioned components are incorporated into the capacitor is not critical and may be accomplished using a variety of techniques. In most embodiments, however, the planar anode is positioned within a casing. The casing may optionally include a lid that covers the anode, cathode, and electrolyte (discussed below), which may be formed from the same or different material than the casing.

Figure 17:
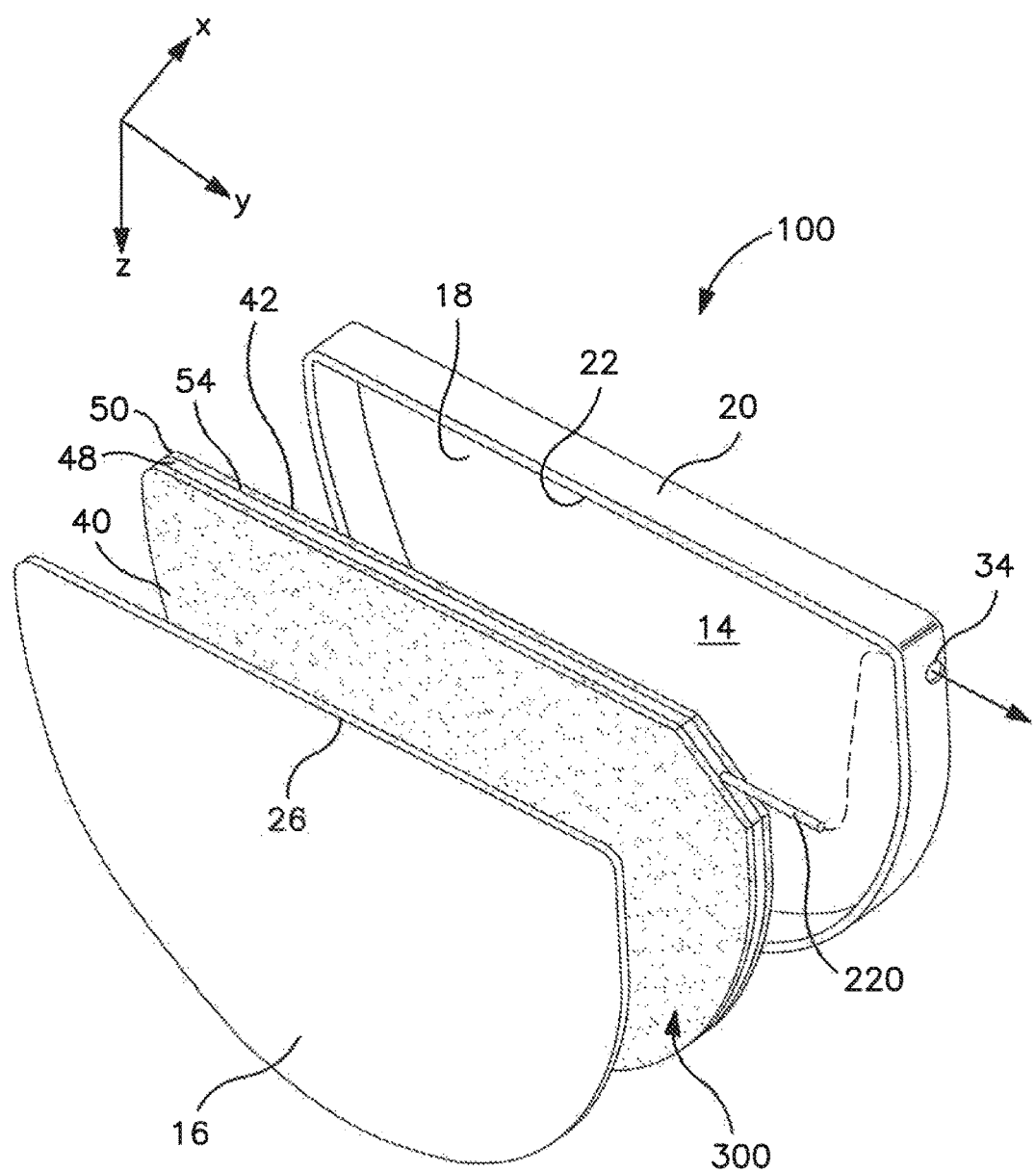
FIG. 17 is an exploded perspective view of the capacitor of FIG. 15 in conjunction with a restraint and a casing.
Figure 18:
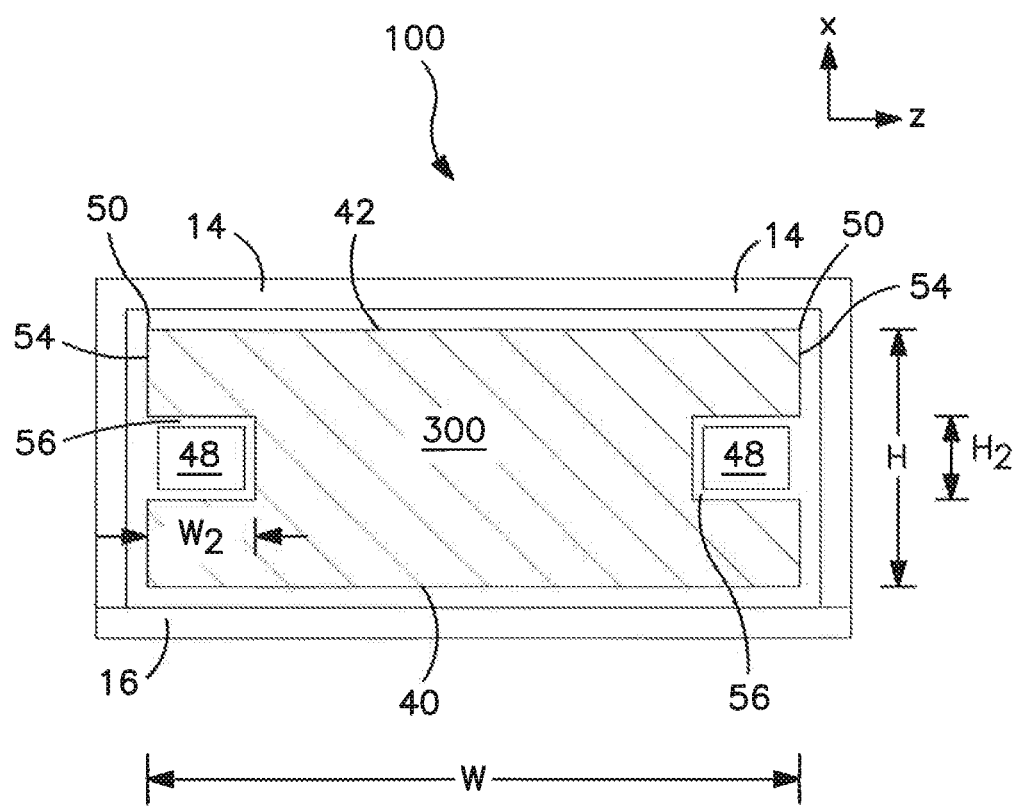
FIG. 18 is a cross-sectional view of the capacitor of FIG. 17 across its width.

Referring to FIGS. 1, 5, 6, and 14, for example, a capacitor 10 is shown that includes the anode 200 shown in FIGS. 2-4 and 7-11 as well as a casing 12. Likewise, FIGS. 15, 17, and 18 show a capacitor 100 that includes the anode 300 shown in FIG. 16 as well as a casing 12. Although only one planar anode is shown, it should be understood that multiple planar anodes (e.g., stack) may be employed as is described, for instance, in U.S. Pat. No. 7,483,260 to Ziarniak, et al. In the illustrated embodiments as shown in FIGS. 1, 5, 6, 14, 15, 17-18, the planar anode 200 or 300 or any other suitable planar anode may be positioned within a casing 12 made of a first casing member 14 and a second casing member 16. The first casing member 14 can have a face wall 18 joined to a surrounding side wall 20 extending to an edge 22. The second casing member 16 can be in the shape of a plate and can contain a second face wall 24 having a surrounding edge 26. The casing members 14 and 16 may be hermetically sealed together by welding (e.g., laser welding) the overlapping edges 22 and 26 where they contact each other. Although not required, the casing members 14 and/or 16 may be analogous to the metal substrate described above such that an electrochemically-active material (e.g., conductive polymer coating) (not shown) may be deposited on the interior surface thereof. Alternatively, a separate metal substrate may be located adjacent to the casing member 14 and/or 16 and applied with the conductive polymer coating to serve as the cathode.

Further, the one or more restraint(s) 48 discussed above can be attached in its desired location to the interior of casing member 14 or casing member 16 by any suitable means, such as via an adhesive or glue (not shown). Alternatively or additionally, the restraint(s) 48 can be attached to the recessed portion 46 or 56 of the anode 200 or 300, respectively, by any suitable means, such as via an adhesive or glue (not shown), in order to lock the anode 200 in place and prevent its movement during use of the capacitor. For example, in order to lock the planar anode 200 of FIGS. 4-7 and 16 in place using the restraint 48, the restraint 48 can be attached to an inner surface of the second casing member 16 and then planar anode 200 can be placed over the inner surface of the second casing member 16 such that the recessed portion 46 of the anode 200 can fit over the restraint 48. Meanwhile, in order to lock the planar anode 300 of FIGS. 15-18 in place using the restraint 48, the restraint 48 can be attached to an inner surface of the first casing member 14 and then the planar anode 300 can angled inside the first casing member 14 such that the recessed portion 56 of the anode 300 can fit over the restraint 48. In another embodiment, the restraints 48 can be attached to the recessed portions 46 or 56 of the planar anodes 200, 201, 202, 203 or 300 and then the planar anodes can places into the first casing member 14. Then, optionally, adhesive or glue can be used on the appropriate casing member 14 or 16 at the area where the restraint 48 will contact the casing member 14 or 16 to ensure that the restraint can lock the planar anode in place. Further, it is to be understood that it is not required that the restraint(s) 48 be attached to the casing member 14, the casing member 16, or the recessed portion 46 or 56, and, instead, the restraint(s) 48 can be injected into the casing 12 at the desired location between the recessed portion 46 or 56 and the casing member 14 or 16 and then allowed to cool to lock the anode 200 or 300 in place inside the casing 12.

In any event, the restraint(s) 48 can be disposed within the recessed portion 46 of anode 200 and recessed portion 56 of anode 300 such that the restraint(s) 48 is generally flush with the sidewall 54 of the planar anode 200 or 300, as shown in FIGS. 14 and 18. As such, the restraint(s) 48 can prevent movement of the planar anode 200 or 300 inside the casing 12. Further, because the restraint(s) 48 is generally flush with the sidewall 54 of the planar anode 200 or 300 and does not extend past the overall thickness "H" or overall width "W" of the planar anode 200 or 300, the size of the casing 12 can be minimized, as shown in FIGS. 14 and 18.

Figure 6:
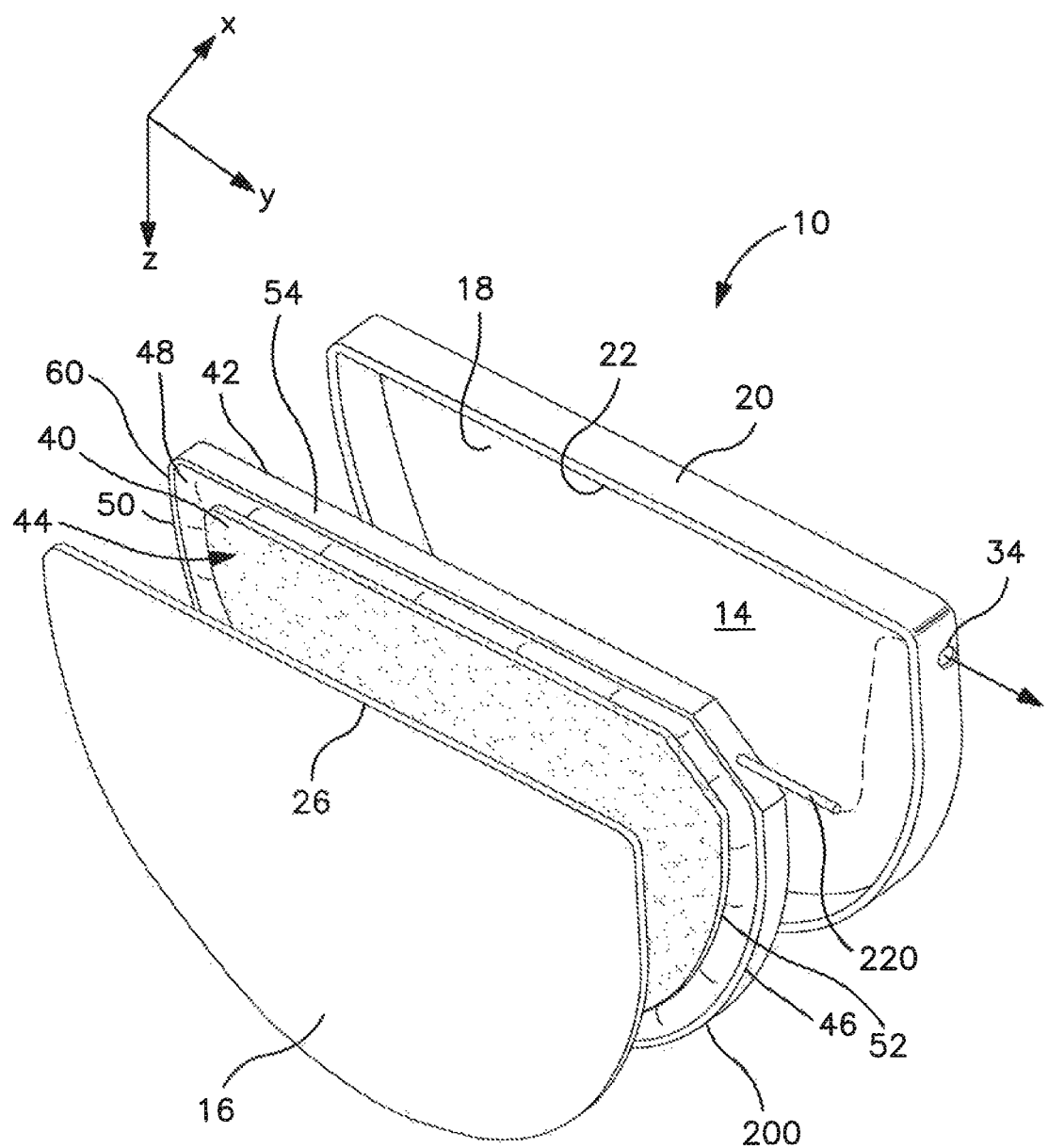
FIG. 6 is an exploded perspective view of the capacitor of FIG. 1 including the planar anode of FIGS. 2 through 4 in conjunction with a restraint and a casing.
Figure 7:
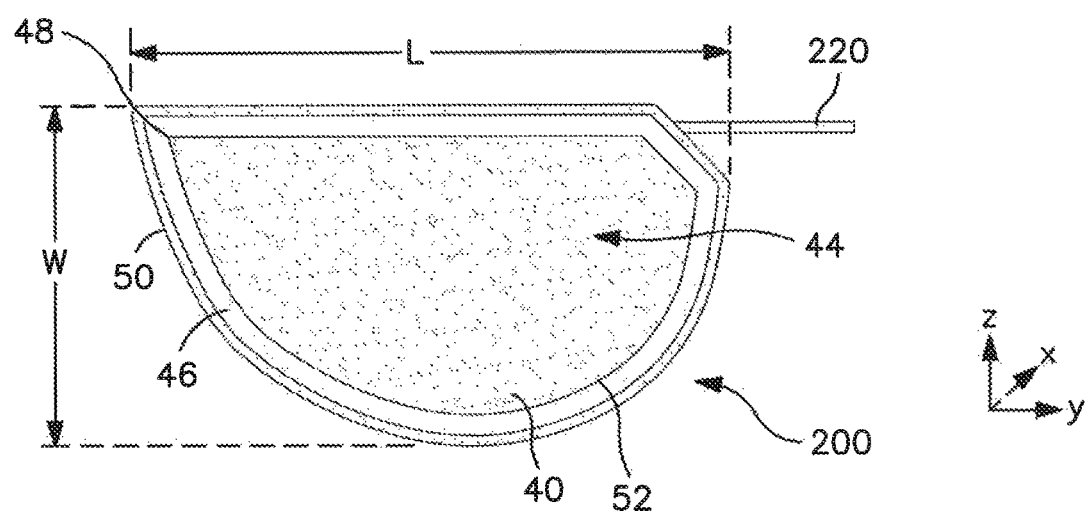
FIG. 7 is a lower surface view of the planar anode and the corresponding restraint in the capacitor of FIG. 6.
Figure 8:
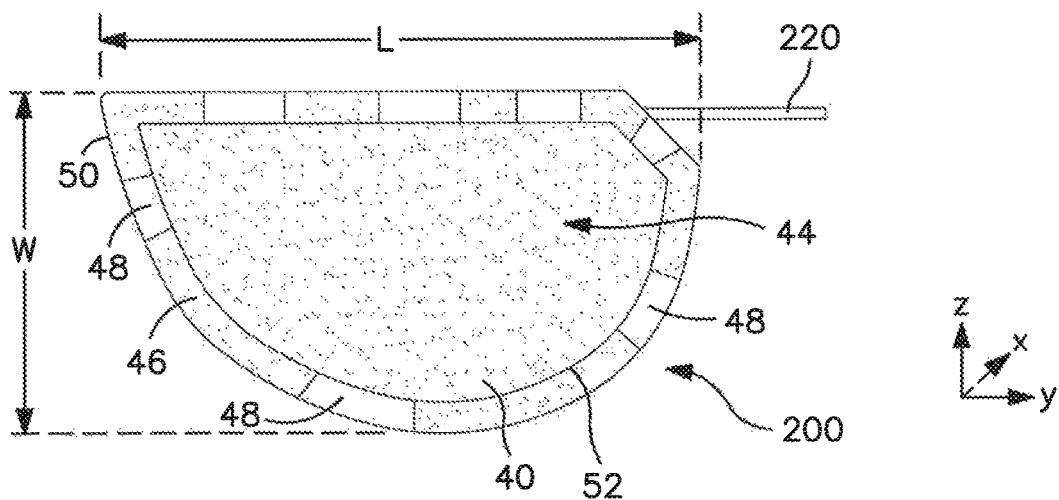
FIG. 8 is a lower surface view of one embodiment of a planar anode and the corresponding restraints that may be employed in the capacitor of the present invention.
Figure 9:
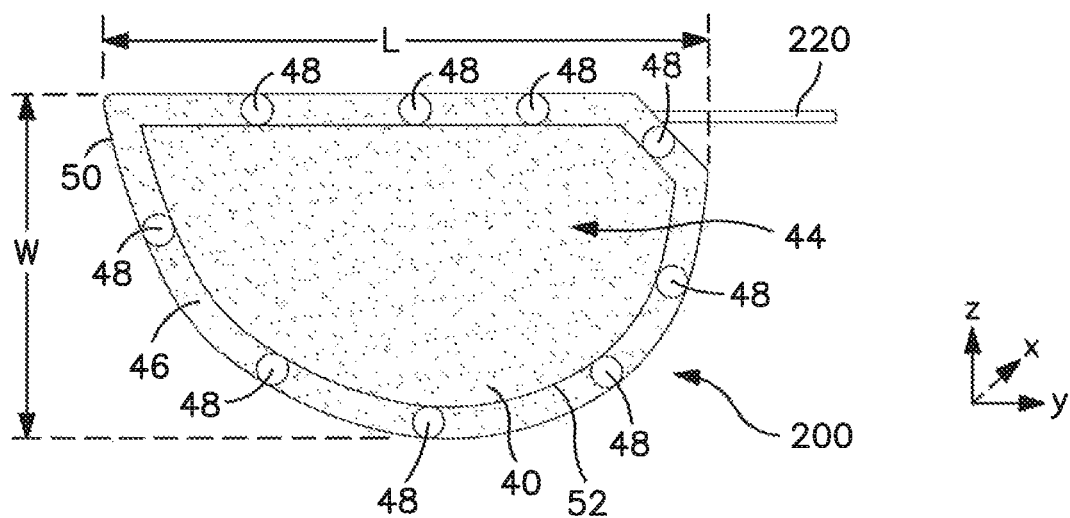
FIG. 9 is a lower surface view of another embodiment of a planar anode and the corresponding restraints that may be employed in the capacitor of the present invention.
Figure 10:
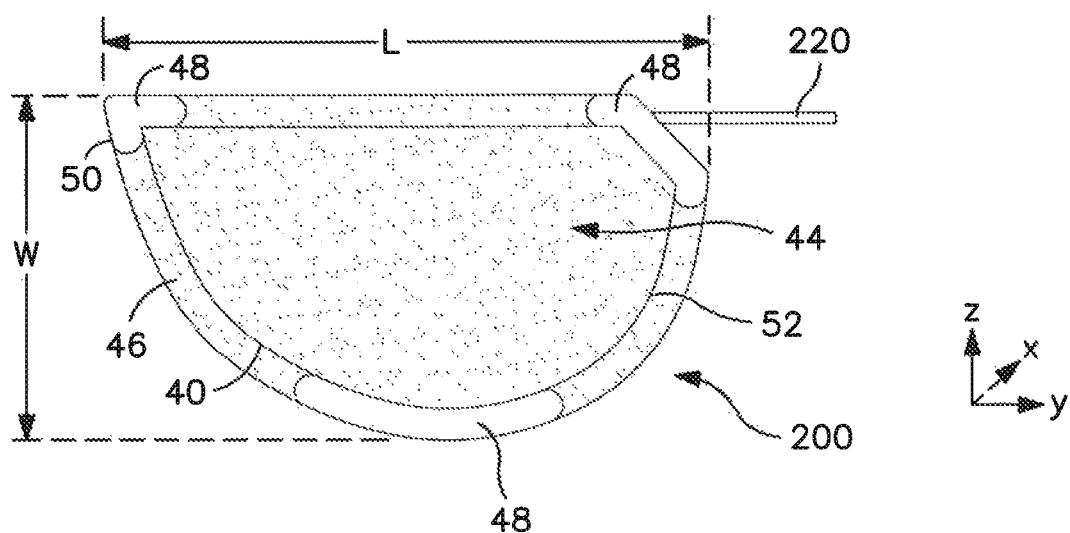
FIG. 10 is a lower surface view of still another embodiment of a planar anode and the corresponding restraints that may be employed in the capacitor of the present invention.

Further, as shown in FIGS. 6-11, the restraint 48 is not limited to a particular shape or configuration so long as the restraint 48 is mated with and can fit inside at least a part of the recessed portion 46 of the anode 200. In one particular embodiment, as shown in FIGS. 6 and 7, the restraint 48 can be in contact with the entire recessed portion 46 of the lower surface 40 of the anode 200 and can have generally the same shape as the shape of the recessed portion 46. Moreover, as shown in FIGS. 12-13, it is not required that the restraint be positioned around the entire periphery of the planar anode 201 or 202. For instance, in FIG. 12, the restraint 48 is only located around part of a recessed portion 46 that extends around the curved portion of the circumferential edge 50 of the planar anode 201 and that does not extend along the straight edge of its length "L." Meanwhile, in FIG. 13, the restraint 48 is only located along a part of straight edge of the length "L" of the planar anode 202 at recessed portion 46. In other words, when one restraint 48 is utilized, it can extend around less than an entire recessed portion 46, such as shown in FIGS. 12 and 13. Further, as shown in FIGS. 14 and 18, the restraint 48 generally does not extend past the height or thickness "H2" of the recessed portion 46 or 56 or beyond the width "W2" of the recessed portion 46 or 56 such that the overall dimensions of the casing 12 can be minimized.

In addition, although the restraint 48 is shown in FIGS. 6 and 7, for example, as a single component that extends around the entire recessed portion 46 at the lower surface 40 of the anode 200 in a continuous fashion, and thus completely surrounds the protruding central portion 44 of the anode 200 at the central protruding portion 44's circumferential inner edge 52, and in FIG. 17 as a single component that extends around the entire recessed portion 56 of the anode 300 at the middle of its side wall 54, this is not required, and instead multiple restraints 48 can be disposed along less than the entire recessed portion 46 in a discontinuous fashion, as shown in FIGS. 8-11. Further, the restraints can be varying shapes such as round, rectangular, square, oblong, triangular, elliptical, etc., as shown in FIGS. 6-13. Regardless of the shape or number of restraints 48 employed, however, the restraints 48 are capable of stabilizing the anode by locking it into place inside casing 12 without increasing the size of the casing 12.

In addition to the components discussed above, although not shown, one or more separators may be employed that help insulate the anode and cathode from each other. Examples of suitable materials for this purpose include, for instance, porous polymer materials (e.g., polypropylene, polyethylene, etc.), porous inorganic materials (e.g., fiberglass mats, porous glass paper, etc.), ion exchange resin materials, etc. Particular examples include ionic perfluorinated sulfonic acid polymer membranes (e.g., Nafion™ from the E.I. DuPont de Nemours & Co.), sulphonated fluorocarbon polymer membranes, polybenzimidazole (PBI) membranes, and polyether ether ketone (PEEK) membranes. Although preventing direct contact between the anode and cathode, the separator permits ionic current flow of the electrolyte to the electrodes.

A feedthrough 30 may also be employed that electrically insulates the anode wire 220 from the casing 12. The feedthrough 30 extends from within the casing 12 to the outside thereof. A hole 34 may be provided in the surrounding side wall 20 of the casing member 14 into which the feedthrough 30 extends. The feedthrough 30 may, for example, be a glass-to-metal seal ("GTMS") that contains a ferrule (not shown) with an internal cylindrical bore of a constant inside diameter. An insulative glass can thus provide a hermetic seal between the bore and the anode wire 220 passing therethrough. After assembly and sealing (e.g., welding), the electrolyte may optionally be introduced into the casing through a fill-port. Filling may be accomplished by placing the capacitor in a vacuum chamber so that the fill-port extends into a reservoir of the electrolyte. When the chamber is evacuated, pressure is reduced inside the capacitor. When the vacuum is released, pressure inside the capacitor re-equilibrates, and the electrolyte is drawn through the fill-port into the capacitor.

IV. Working Electrolyte

The capacitor of the present invention also employs a working electrolyte that is disposed inside the casing and is the electrically active material that provides the connecting path between the anode and cathode. The working electrolyte can generally be in the form of a liquid, such as a solution (e.g., aqueous or non-aqueous), dispersion, gel, etc. If desired, the anode may initially be impregnated with an electrolyte (not shown) before being positioned within the casing. The electrolyte may also be added to the capacitor at a later stage of production. Various suitable electrolytes are described in U.S. Pat. Nos. 5,369,547 and 6,594,140 to Evans, et al, which are incorporated herein their entirety by reference thereto for all purposes.

Typically, the electrolyte is ionically conductive in that has an ionic conductivity of from about 1 to about 100 milliSiemens per centimeter ("mS/cm"), in some embodiments from about 5 to about 80 mS/cm, in some embodiments from about 15 mS/cm to about 70 mS/cm, and in some embodiments, from about 20 to about 60 mS/cm, determined at a temperature of 25° C. using any known electric conductivity meter (e.g., Oakton Con Series 11). Within the ranges noted, the electric field is strong as the dielectric but can extend into the electrolyte to a length (Debye length) sufficient to result in significant charge separation. This extends the potential energy of the dielectric to the electrolyte so that the resulting capacitor is able to store even more potential energy than predicted by the thickness of the dielectric. In other words, the capacitor may be charged to a voltage that is close to or even exceeds the formation voltage of the dielectric. The ratio of the voltage to which the capacitor can be charged to the formation voltage may, for instance, be from about 0.80 to about 2.00, and in some embodiments, from about 0.85 to about 1.50, and in some embodiments, from about 0.86 to about 1.20. As an example, the voltage to which the capacitor is charged may be from about 150 volts to about 300 volts, in some embodiments from about 180 volts to about 260 volts, and in some embodiments, from about 200 volts to about 240 volts. The formation voltage may likewise range from about from about 180 volts to about 320 volts, in some embodiments from about 200 volts to about 280 volts, and in some embodiments, from about 220 volts to about 250 volts. The working electrolyte is also relatively neutral and thus has a pH value of from about 4.5 to about 8.0, in some embodiments from about 5.0 to about 7.5, in some embodiments, from about 5.5 to about 7.0, and in some embodiments from about 6.0 to about 6.5. Among other things, such a pH may enhance the ability of hydrogen ions present in an aqueous electrolyte to interact with the cathode material to achieve maximum capacitance and thus energy density.

The desired ionic conductivity may be achieved by selecting ionic compound(s) (e.g., acids, bases, salts, and so forth) within certain concentration ranges. In one particular embodiment, salts of weak organic acids may be effective in achieving the desired conductivity of the electrolyte. The cation of the salt may include monatomic cations, such as alkali metals (e.g., $Li^+$, $Na^+$, $K^+$, $Rb^+$, or $Cs^+$), alkaline earth metals (e.g., $Be^{2+}$, $Mg^{2+}$, $Ca^{2+}$, $Sr^{2+}$ or $Ba^{2+}$), transition metals (e.g., $Ag^+$, $Fe^{2+}$, $Fe^{3+}$, etc.), as well as polyatomic cations, such as $NH_4$. The monovalent ammonium ($NH_4^+$), sodium ($K^+$), and lithium ($Li^+$) are particularly suitable cations for use in the present invention. The organic acid used to form the anion of the salt is "weak" in the sense that it typically has a first acid dissociation constant ($pK_{a1}$) of about 0 to about 11, in some embodiments about 1 to about 10, and in some embodiments, from about 2 to about 10, determined at 25° C. Any suitable weak organic acids may be used in the present invention, such as carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid (e.g., dextotartaric acid, mesotartaric acid, etc.), citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; blends thereof, and so forth. Polyprotic acids (e.g., diprotic, triprotic, etc.) are particularly desirable for use in forming the salt, such as adipic acid ($pK_{a1}$ of 4.43 and $pK_{a2}$ of 5.41), α-tartaric acid ($pK_{a1}$ of 2.98 and $pK_{a2}$ of 4.34), meso-tartaric acid ($pK_{a1}$ of 3.22 and $pK_{a2}$ of 4.82), oxalic acid ($pK_{a1}$ of 1.23 and $pK_{a2}$ of 4.19), lactic acid ($pK_{a1}$ of 3.13, $pK_{a2}$ of 4.76, and $pK_{a3}$ of 6.40), etc.

While the actual amounts may vary depending on the particular salt employed, its solubility in the solvent(s) used in the electrolyte, and the presence of other components, such weak organic acid salts are typically present in the electrolyte in an amount of from about 0.1 to about 40 wt. %, in some embodiments from about 0.2 to about 35 wt. %, in some embodiments from about 0.3 to about 30 wt. %, and in some embodiments, from about 0.5 to about 25 wt. %.

The electrolyte is typically aqueous in that it contains an aqueous solvent, such as water (e.g., deionized water). For example, water (e.g., deionized water) may constitute from about 20 wt. % to about 95 wt. %, in some embodiments from about 30 wt. % to about 90 wt. %, and in some embodiments, from about 40 wt. % to about 85 wt. % of the electrolyte. A secondary solvent may also be employed to form a solvent mixture. Suitable secondary solvents may include, for instance, glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); alcohols (e.g., methanol, ethanol, n-propanol, iso-propanol, and butanol); ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate, etc.); amides (e.g., dimethylformamide, dimethylacetamide, dimethylcaprylic/capric fatty acid amide and N-alkylpyrrolidones); sulfoxides or sulfones (e.g., dimethyl sulfoxide (DMSO) and sulfolane); and so forth. Such mixtures typically contain water in an amount from about 40 wt. % to about 80 wt. %, in some embodiments from about 50 wt. % to about 75 wt. %, and in some embodiments, from about 60 wt. % to about 70 wt. % of the solvent system and secondary solvents in an amount from about 20 wt. % to about 60 wt. %, in some embodiments from about 25 wt. % to about 50 wt. %, and in some embodiments, from about 30 wt. % to about 40 wt.

% of the solvent system. Likewise, when such mixtures are employed, water typically constitutes from about 30 wt. % to about 70 wt. %, in some embodiments from about 35 wt. % to about 65 wt. %, and in some embodiments, from about 40 wt. % to about 60 wt. % of the electrolyte and secondary solvents may constitute from about 5 wt. % to about 40 wt. %, in some embodiments from about 10 wt. % to about 35 wt. %, and in some embodiments, from about 15 wt. % to about 30 wt. % of the electrolyte.

One or more acids or pH adjusters are also employed to help achieve the desired pH and conductivity values. Suitable acids may include, for instance, inorganic acids, such as hydrochloric acid, nitric acid, sulfuric acid, phosphoric acid, polyphosphoric acid, boric acid, boronic acid, etc.; organic acids, including carboxylic acids, such as acrylic acid, methacrylic acid, malonic acid, succinic acid, salicylic acid, sulfosalicylic acid, adipic acid, maleic acid, malic acid, oleic acid, garlic acid, tartaric acid, citric acid, formic acid, acetic acid, ethylenediaminetetraacetic acid ("EDTA"), glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; sulfonic acids, such as methanesulfonic acid, benzenesulfonic acid, toluenesulfonic acid, trifluoromethanesulfonic acid, styrenesulfonic acid, naphthalene disulfonic acid, hydroxybenzenesulfonic acid, etc.; polymeric acids, such as poly(acrylic) or poly(methacrylic) acid and copolymers thereof (e.g., maleic-acrylic, sulfonic-acrylic, and styrene-acrylic copolymers), carageenic acid, carboxymethyl cellulose, alginic acid, etc.; and so forth. EDTA may be particularly suitable when a gelled electrolyte is used as it not only can reduce the pH value of the electrolyte, but it can also serve as a sequestering agent for any metallic impurities that may be present in the particles.

Although the total concentration of acids may vary, they are typically present in an amount of from about 0.01 wt. % to about 10 wt. %, in some embodiments from about 0.05 wt. % to about 5 wt. %, and in some embodiments, from about 0.1 wt. % to about 2 wt % of the electrolyte. In one particular embodiment, a mixture of different acids may be employed, such as mixture of an inorganic and an organic acid. In such embodiments, inorganic acids (e.g., phosphoric acid) may constitute from about 0.005 wt. % to about 5 wt. %, in some embodiments from about 0.01 wt. % to about 3 wt. %, and in some embodiments from about 0.05 wt. % to about 1 wt. % of the electrolyte, and organic acids (e.g., EDTA) may likewise constitute from about 0.005 wt. % to about 5 wt. %, in some embodiments from about 0.01 wt. % to about 3 wt. %, and in some embodiments, from about 0.05 wt. % to about 1 wt. % of the electrolyte.

The electrolyte may also contain other components that help improve the electrical performance of the capacitor. For instance, a depolarizer may be employed in the electrolyte to help inhibit the evolution of hydrogen gas at the cathode of the electrolytic capacitor, which could otherwise cause the capacitor to bulge and eventually fail. When employed, the depolarizer normally constitutes from about 1 to about 500 parts per million ("ppm"), in some embodiments from about 10 to about 200 ppm, and in some embodiments, from about 20 to about 150 ppm of the electrolyte. For instance, the depolarizers normally constitute from about 0.01 wt. % to about 5 wt. %, in some embodiments from about 0.05 wt. % to about 2 wt. %, and in some embodiments from about 0.1 wt. % to about 1 wt. % of the electrolyte.

Suitable depolarizers may include nitroaromatic compounds, such as 2-nitrophenol, 3-nitrophenol, 4-nitrophenol, 2-nitrobenzonic acid, 3-nitrobenzonic acid, 4-nitrobenzonic acid, 2-nitroace tophenone, 3-nitroacetophenone, 4-nitroacetophenone, 2-nitroanisole, 3-nitroanisole, 4-nitroanisole, 2-nitrobenzaldehyde, 3-nitrobenzaldehyde, 4-nitrobenzaldehyde, 2-nitrobenzyl alcohol, 3-nitrobenzyl alcohol, 4-nitrobenzyl alcohol, 2-nitrophthalic acid, 3-nitrophthalic acid, 4-nitrophthalic acid, and so forth. Particularly suitable nitroaromatic depolarizers for use in the present invention are nitrobenzoic acids, anhydrides or salts thereof, substituted with one or more alkyl groups (e.g., methyl, ethyl, propyl, butyl, etc). Specific examples of such alkyl-substituted nitrobenzoic compounds include, for instance, 2-methyl-3-nitrobenzoic acid; 2-methyl-6-nitrobenzoic acid; 3-methyl-2-nitrobenzoic acid; 3-methyl-4-nitrobenzoic acid; 3-methyl-6-nitrobenzoic acid; 4-methyl-3-nitrobenzoic acid; anhydrides or salts thereof; and so forth.

In one particular embodiment, the working electrolyte can be in the form of a viscoelastic "gel", which is generally defined as a solid or semi-solid colloidal suspension that contains a continuous phase and a dispersed phase, wherein at least one of the phases is a solid and at least one of the phases is a liquid. For example, a hydrogel may be formed when the inorganic oxide particles are crosslinked to form a continuous phase and the solvent contains water as a disperse phase that is entrapped within the crosslinked network. Regardless of its exact form, the viscoelastic gel within the capacitor is in the form of a semi-solid or solid so that it is not readily flowable at room temperature. This property can be represented by the viscoelastic phase angle $\delta$, which is the degree to which the sinusoidal time variation in the stress is out of phase with the sinusoidal time variation in the shear rate. The phase angle $\delta$ for an ideal elastic solid is 0° (in phase) and the phase angle $\delta$ for an ideal viscous liquid is 90° (out of phase). In the present invention, the gelled electrolyte typically exhibits a phase angle $\delta$ of from 0° to about 20°, in some embodiments from 0.1° to about 5°, and in some embodiments, from about 0.2° to about 2°. Another parameter that can represent the viscoelastic behavior of the gel is the storage modulus, G', which is determined by dividing the "in-phase" component of the stress (representing solid-like behavior) by the maximum strain. Typically, the gelled electrolyte of the present invention exhibits a storage modulus of about 5 kilopascals ("kPa") or more, in some embodiments about 10 kPa or more, and in some embodiments from about 15 to about 50 kPa. The phase angle and storage modulus can be determined at room temperature (e.g., 25° C.) by dynamic oscillatory testing (e.g., frequency of 10 Hz and pressure of 5 Pa) with a rheometer having a cone plate configuration.

To achieve the combination of high conductivity and a neutral pH value, the gel working electrolyte can contain a combination of the weak organic acid salt, solvent system, and pH adjuster (acid) discussed above in conjunction with inorganic oxide particles to help achieve the desired viscosity and electrical properties for the capacitor.

The amount of inorganic oxide particles in the electrolyte may vary depending on the degree of gelation required, as well as the particular nature and concentration of other components in the electrolyte. Typically, however, inorganic oxide particles constitute from about 0.5 wt. % to about 20 wt. %, in some embodiments from about 1 wt % to about 15 wt. %, and in some embodiments, from about 1.5 wt. % to about 10 wt. % of the electrolyte.

The particles may possess various forms, shapes, and sizes depending upon the desired result. For instance, the particles may be in the shape of a sphere, crystal, rod, disk, tube, string, etc. The average size of the particles may be less than about 1,000 nanometers, in some embodiments from about 1 to about 500 nanometers, in some embodiments from about 2 to about 200 nanometers, and in some embodiments, from about 4 to about 50 nanometers. As used herein, the average size of a particle refers to its average length, width, height, and/or diameter. The particles also typically have a high specific surface area, such as from about 50 square meters per gram ($m^2/g$) to about 1000 $m^2/g$, in some embodiments from about 100 $m^2/g$ to about 600 $m^2/g$, and in some embodiments, from about 150 $m^2/g$ to about 400 $m^2/g$. The term "specific surface area" generally refers to surface area as determined by the physical gas adsorption (B.E.T.) method of Bruanauer, Emmet, and Teller, Journal of American Chemical Society, Vol. 60, 1938, p. 309, with nitrogen as the adsorption gas. The test may be conducted with a MONOSORB® Specific Surface Area Analyzer available from QUANTACHROME Corporation, Syosset, N.Y., which measures the quantity of adsorbate nitrogen gas adsorbed on a solid surface by sensing the change in thermal conductivity of a flowing mixture of adsorbate and inert carrier gas (e.g., helium). In addition, the particles may also be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. Without intending to be limited by theory, it is believed that particles having such a small size, high surface area, and solid nature may improve the gelation rate and enhance the uniformity and stability of the resulting suspension.

The inorganic oxide particles may be formed from a variety of materials, including, but not limited to, silica, alumina, zirconia, magnesium oxide, titanium dioxide, iron oxide, zinc oxide, copper oxide, etc., as well as combinations thereof. The particles may also be formed using a fumed process, precipitation, etc. Due to their higher surface area and smaller particle size, however, fumed particles are particularly suitable for use in the present invention. Fumed silica, for instance, is amorphous $SiO_2$ that can be produced by vapor phase hydrolysis of silicon tetrachloride in a hydrogen oxygen flame. Three-dimensional branched chain aggregates are produced in the flame from fusion of the primary particles. During cooling, these aggregates agglomerate into a fine powder having a particle size within the ranges noted above. Fumed silica possesses silanol groups that can react under acidic conditions to form a cross-linked network. The resulting siloxane cross-linkage is a compound of silicon and oxygen in which each atom of silicon is bonded to four oxygen atoms, forming a tetrahedral structure, in a manner analogous to the bonding of carbon to hydrogen in methane, the bonds being of about the same strength in each case. This structure is found in the dioxide and in silicates generally, where the $SiO_4$ groups occur in chains or rings. By creating siloxane cross-linkages, a gel is formed that entraps the liquid phase of the electrolyte. Commercially suitable fumed silica particles may, for instance, include those available from Cabot Corporation under the designation CAB-O-SIL®.

The components of the working electrolyte can be combined together in a variety of different ways, either before and/or after their incorporation into the capacitor. In one particular embodiment, the electrolyte may be gelled before it is placed into contact with the anode and/or cathode. For example, when the components of the electrolyte are initially combined together, the electrolyte may be in the form of a sol that contains particles as a disperse phase. However, such sols can be catalyzed to induce gelation by several methods. Examples include adjusting the pH and/or temperature of the sol to a point where gelation occurs. Alternatively, the sol may be subjected to a controlled form of energy (e.g., heat, ultrasonic, ultraviolet light, electron beam radiation, etc.) to induce gelation. The use of ultrasonic energy (e.g., ultrasonic probes) is particularly desirable as it minimizes the need to alter the pH or temperature of the electrolyte.

The electrolyte can be incorporated into the capacitor in a variety of different ways. In one embodiment, for example, the electrolyte is simply added to the capacitor after the anode and cathode are positioned in the desired configuration. This may be accomplished, for instance, using a fill port. The anode may also be pre-impregnated with the electrolyte, such as by dipping the anode into the electrolyte before it is placed into the capacitor. Impregnation of the anode with the electrolyte can further enhance the degree of contact between the anode and the electrolyte. The electrolyte can have a low initial viscosity and flowability so that it can be precisely incorporated into the capacitor. For example, when in the form of a gel, the electrolyte may have an initial viscosity (e.g., 1 hour or less after gelation is initiated) within the range of from about 1 to about 40 centipoise, in some embodiments from about 2 to about 30 centipoise, and in some embodiments, from about 3 to about 10 centipoise, as determined using a Brookfield LVT viscometer (spindle #3 at 60 rpm) at a temperature of 25° C. Likewise, the gel may have an initial phase angle δ of from about 50° to 90°, in some embodiments from about 60° to 90°, and in some embodiments, from about 80° to 90°, as well as an initial storage modulus G' of about 1 kilopascal or less, in some embodiments about 0.1 kilopascals or less, and in some embodiments, from 0 to about 0.01 kilopascals.

After incorporation into the capacitor, however, the electrolyte may continue to gel until the viscosity is raised, such as to a viscosity, phase angle δ, and/or storage modulus G' within the target ranges noted above. This "semi-solid" or "solid" transition may occur relatively after gelation is induced, such as from about 1 to about 100 hours, in some embodiments from about 10 to about 80 hours, and in some embodiments, from about 20 to about 60 hours. The transition may also occur before and/or after the anode is incorporated into the capacitor and placed in contact with the cathode. If desired, an additional "fill" electrolyte may be added to ensure that good electrical contact exists between the impregnated anode and the cathode. This fill electrolyte may be formed in accordance with the present invention, or it may be formed from other known components.

Regardless of its particular configuration, the capacitor of the present invention may exhibit excellent electrical properties. For example, the capacitor may exhibit a high volumetric efficiency, such as from about 50,000 $\mu F*V/cm^3$ to about 300,000 $\mu F*V/cm^3$, in some embodiments from about 60,000 $\mu F*V/cm^3$ to about 200,000 $\mu F*V/cm^3$, and in some embodiments, from about 80,000 $\mu F*V/cm^3$ to about 150,000 $\mu F*V/cm^3$, determined at a frequency of 120 Hz and at room temperature (e.g., 25° C.). Volumetric efficiency is determined by multiplying the formation voltage of a part by its capacitance, and then dividing by the product by the volume of the part. For example, a formation voltage may be 175 volts for a part having a capacitance of 520 μF, which results in a product of 91,000 μF*V. If the part occupies a volume of about 0.8 $cm^3$, this results in a volumetric efficiency of about 113,750 $\mu F*V/cm^3$.

The capacitor may also exhibit a high energy density that enables it suitable for use in high pulse applications. Energy density is generally determined according to the equation $E=\frac{1}{2}*CV^2$, where C is the capacitance in farads (F) and V is the working voltage of capacitor in volts (V). The capacitance may, for instance, be measured using a capacitance meter (e.g., Keithley 3330 Precision LCZ meter with Kelvin Leads, 2 volts bias and 1 volt signal) at operating frequencies of from 10 to 120 Hz (e.g., 120 Hz) and a temperature of 25° C. For example, the capacitor may exhibit an energy density of about 2.0 joules per cubic centimeter ($J/cm^3$) or more, in some embodiments about 3.0 $J/cm^3$, in some embodiments from about 3.5 $J/cm^3$ to about 15.0 $J/cm^3$, and in some embodiments, from about 4.0 to about 12.0 $J/cm^3$. The capacitance may likewise be about 1 milliFarad per square centimeter ("$mF/cm^2$") or more, in some embodiments about 2 $mF/cm^2$ or more, in some embodiments from about 5 to about 50 $mF/cm^2$, and in some embodiments, from about 8 to about 20 $mF/cm^2$. The capacitor may also exhibit a relatively high "breakdown voltage" (voltage at which the capacitor fails), such as about 180 volts or more, in some embodiments about 200 volts or more, and in some embodiments, from about 210 volts to about 260 volts.

The equivalent series resistance ("ESR")—the extent that the capacitor acts like a resistor when charging and discharging in an electronic circuit—may also be less than about 15,000 milliohms, in some embodiments less than about 10,000 milliohms, in some embodiments less than about 5,000 milliohms, and in some embodiments, from about 1 to about 4,500 milliohms, measured with a 2-volt bias and 1-volt signal at a frequency of 120 Hz. In addition, the leakage current, which generally refers to the current flowing from one conductor to an adjacent conductor through an insulator, can be maintained at relatively low levels. For example, the numerical value of the normalized leakage current of a capacitor of the present invention is, in some embodiments, less than about 1 $\mu A/\mu F*V$, in some embodiments less than about 0.5 $\mu A/\mu F*V$, and in some embodiments, less than about 0.1 $\mu A/\mu F*V$, where $\mu A$ is microamps and $\mu F*V$ is the product of the capacitance and the rated voltage. Leakage current may be measured using a leakage test meter (e.g., MC 190 Leakage test, Mantracourt Electronics LTD, UK) at a temperature of 25° C. and at a certain rated voltage after a charging time of from about 60 to about 300 seconds. Such ESR and normalized leakage current values may even be maintained after aging for a substantial amount of time at high temperatures. For example, the values may be maintained for about 100 hours or more, in some embodiments from about 300 hours to about 2500 hours, and in some embodiments, from about 400 hours to about 1500 hours (e.g., 500 hours, 600 hours, 700 hours, 800 hours, 900 hours, 1000 hours, 1100 hours, or 1200 hours) at temperatures ranging from about 100° C. to about 250° C., and, in some embodiments from about 100° C. to about 200° C. (e.g., 100° C., 125° C., 150° C., 175° C., or 200° C.).

The electrolytic capacitor of the present invention may be used in various applications, including but not limited to medical devices, such as implantable defibrillators, pacemakers, cardioverters, neural stimulators, drug administering devices, etc.; automotive applications; military applications, such as RADAR systems; consumer electronics, such as radios, televisions, etc.; and so forth. In one embodiment, for example, the capacitor may be employed in an implantable medical device configured to provide a therapeutic high voltage (e.g., between approximately 500 volts and approximately 850 volts, or, desirably, between approximately 600 Volts and approximately 900 volts) treatment for a patient. The device may contain a container or housing that is hermetically sealed and biologically inert. One or more leads are electrically coupled between the device and the patient's heart via a vein. Cardiac electrodes are provided to sense cardiac activity and/or provide a voltage to the heart. At least a portion of the leads (e.g., an end portion of the leads) may be provided adjacent or in contact with one or more of a ventricle and an atrium of the heart. The device may also contain a capacitor bank that typically contains two or more capacitors connected in series and coupled to a battery that is internal or external to the device and supplies energy to the capacitor bank. Due in part to high conductivity, the capacitor of the present invention can achieve excellent electrical properties and thus be suitable for use in the capacitor bank of the implantable medical device.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A wet electrolytic capacitor comprising:
   a planar anode having an outer periphery and comprising an anodically oxidized pellet formed from a pressed and sintered powder, the planar anode having a recessed portion formed in at least one surface;
   a cathode that comprises a metal substrate coated with an electrochemically-active material;
   a restraint, in direct contact with the anode, that fits within the recessed portion and has a shape that generally corresponds with a shape of the recessed portion such that the restraint does not extend beyond the outer periphery of the anode; and
   a working electrolyte in communication with the planar anode and the cathode.

2. The wet electrolytic capacitor of claim 1, wherein the restraint is in contact with the entire recessed portion of the planar anode.

3. The wet electrolytic capacitor of claim 1, wherein multiple restraints are in contact with multiple sections of the recessed portion of the planar anode.

4. The wet electrolytic capacitor of claim 1, wherein the restraint comprises a polymer, a glass, or a ceramic.

5. The wet electrolytic capacitor of claim 4, wherein the restraint comprises a polyolefin, a fluoropolymer, an elastomer, a curable thermosetting resin, an epoxy resin, or a combination thereof.

6. The wet electrolytic capacitor of claim 1, wherein the recessed portion is formed in an upper surface or a lower surface of the planar anode.

7. The wet electrolytic capacitor of claim 6, wherein the recessed portion extends from a circumferential inner edge of the planar anode to a circumferential outer edge of the planar anode, the circumferential inner edge defining a protruding central portion of the planar anode.

8. The wet electrolytic capacitor of claim 7, wherein the protruding central portion has a surface area that is from about 50% to about 99.5% of a surface area of the planar anode defined by the circumferential outer edge.

9. The wet electrolytic capacitor of claim 7, wherein the restraint is in contact with the circumferential inner edge of the planar anode.

10. The wet electrolytic capacitor of claim 7, wherein the circumferential inner edge of the planar anode and the circumferential outer edge of the planar anode have generally the same shape.

11. The wet electrolytic capacitor of claim 7, wherein the circumferential inner edge has a different shape from the circumferential outer edge of the planar anode.

12. The wet electrolytic capacitor of claim 1, wherein the recessed portion is formed in a side wall of the planar anode.

13. The wet electrolytic capacitor of claim 12, wherein an upper surface and a lower surface of the planar anode have the same shape and dimensions.

14. The wet electrolytic capacitor of claim 1, wherein the planar anode has a D-shape.

15. The wet electrolytic capacitor of claim 1, wherein the planar anode has a stepped shape.

16. The wet electrolytic capacitor of claim 1, wherein the electrochemically-active material comprises a conductive polymer.

17. The wet electrolytic capacitor of claim 16, wherein the conductive polymer is a substituted polythiophene.

18. The wet electrolytic capacitor of claim 1, wherein the planar anode has a thickness of about 5 millimeters or less.

19. The wet electrolytic capacitor of claim 1, wherein the powder is formed from tantalum particles.

20. The wet electrolytic capacitor of claim 1, wherein the metal substrate includes titanium.

21. The wet electrolytic capacitor of claim 1, wherein the metal substrate forms a casing around the planar anode.

22. An implantable medical device comprising the wet electrolytic capacitor of claim 1.

23. A planar anode for a wet electrolytic capacitor, the planar anode having an outer periphery and comprising an anodically oxidized pellet formed from a pressed and sintered powder, wherein a recessed portion is located in a surface of the planar anode, wherein the recessed portion is configured to receive a restraint, in direct contact with the anode, that fits within the recessed portion such that the restraint does not extend beyond the outer periphery of the anode.

24. An implantable medical device comprising the planar anode of claim 23.

* * * * *